(12) United States Patent
Scott et al.

(10) Patent No.: US 7,806,915 B2
(45) Date of Patent: Oct. 5, 2010

(54) APPARATUS AND METHOD FOR PROVIDING ENHANCED HEAT TRANSFER FROM A BODY

(75) Inventors: David J. Scott, Redwood City, CA (US); Ben F. Brian, Menlo Park, CA (US); Lloyd F. Wright, Hopewell Junction, NY (US); Leo A. Chin, Poughquag, NY (US); Edward W. Hollmen, Poughkeepsie, NY (US); Daniel W. Seegars, Salt Point, NY (US); Mark A. Logan, Pleasant Valley, NY (US)

(73) Assignee: Zoll Circulation, Inc., Sunnyvale, CA (US)

( * ) Notice: Subject to any disclaimer, the term of this patent is extended or adjusted under 35 U.S.C. 154(b) by 1085 days.

(21) Appl. No.: 11/413,564

(22) Filed: Apr. 27, 2006

(65) Prior Publication Data

US 2006/0293734 A1 Dec. 28, 2006

Related U.S. Application Data

(60) Provisional application No. 60/695,800, filed on Jun. 29, 2005, provisional application No. 60/594,662, filed on Apr. 27, 2005.

(51) Int. Cl.
*A61F 7/00* (2006.01)
(52) U.S. Cl. ............................ 607/106; 607/96; 607/104
(58) Field of Classification Search .................... 607/96, 607/102, 104–107; 604/27–30, 93.01, 113, 604/506–508
See application file for complete search history.

(56) References Cited

U.S. PATENT DOCUMENTS 3,007,473 A 11/1961 Jackson et al.
3,074,410 A 1/1963 Foster
3,369,549 A 2/1968 Armao (Continued)

FOREIGN PATENT DOCUMENTS

WO WO 97/39707 10/1997

(Continued)

OTHER PUBLICATIONS

International Search Report, Aug. 3, 2007.

(Continued)

*Primary Examiner*—Ahmed M Farah
(74) *Attorney, Agent, or Firm*—John K. Fitzgerald; Fulwider Patton LLP

(57) ABSTRACT

Methods and apparatuses for temperature modification of a patient, or selected regions thereof, including an induced state of hypothermia. The temperature modification is accomplished using an in-dwelling heat exchange catheter within which a fluid heat exchange medium circulates. A heat exchange cassette is attached to the circulatory conduits of the catheter, the heat exchange cassette being sized to engage a cavity within a control unit. The control unit includes a heater/cooler device for providing heated or cooled fluid to a heat exchanger in thermal communication with the fluid heat exchange medium circulating to the heat exchange catheter, a user input device, and a processor connected to receive input from various sensors around the body and the system. A temperature control scheme for ramping the body temperature up or down without overshoot is provided.

48 Claims, 15 Drawing Sheets

U.S. PATENT DOCUMENTS

| | | | |
|---|---|---|---|
| 3,504,674 A | 4/1970 | Swenson et al. |
| 3,626,670 A | 12/1971 | Pecker |
| 3,661,262 A | 5/1972 | Sanders |
| 4,026,581 A | 5/1977 | Pasbrig |
| 4,111,209 A | 9/1978 | Wolvek et al. |
| 4,459,468 A | 7/1984 | Bailey |
| 4,665,391 A | 5/1987 | Spani |
| 4,692,251 A | 9/1987 | Hilgren |
| 4,767,289 A | 8/1988 | Parrot et al. |
| 4,881,487 A | 11/1989 | Moore |
| 4,919,134 A | 4/1990 | Streeter |
| 4,941,475 A | 7/1990 | Williams et al. |
| 4,960,103 A | 10/1990 | Urso |
| 4,962,761 A | 10/1990 | Golden |
| 5,097,829 A | 3/1992 | Quisenberry |
| 5,174,285 A | 12/1992 | Fontenot |
| 5,211,631 A | 5/1993 | Sheaff |
| 5,330,519 A | 7/1994 | Mason et al. |
| 5,342,182 A | 8/1994 | Montoya et al. |
| 5,344,436 A | 9/1994 | Fontenot et al. |
| 5,387,088 A | 2/1995 | Knapp et al. |
| 5,476,368 A | 12/1995 | Rabenau et al. |
| 5,486,208 A | 1/1996 | Ginsburg |
| 5,514,094 A | 5/1996 | Anello et al. |
| 5,624,392 A | 4/1997 | Saab |
| 5,645,531 A | 7/1997 | Thompson et al. |
| 5,716,386 A | 2/1998 | Ward et al. |
| 5,733,319 A | 3/1998 | Neilson et al. |
| 5,837,003 A | 11/1998 | Ginsburg |
| 5,871,526 A | 2/1999 | Gibbs et al. |
| 5,879,329 A | 3/1999 | Ginsburg |
| 5,895,418 A | 4/1999 | Saringer |
| 5,957,963 A | 9/1999 | Dobak, III |
| 5,965,089 A | 10/1999 | Jarvik et al. |
| 5,972,013 A | 10/1999 | Schmidt |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak, III |
| 6,051,019 A | 4/2000 | Dobak, III |
| 6,096,068 A | 8/2000 | Dobak, III et al. |
| 6,126,684 A | 10/2000 | Gobin et al. |
| 6,146,411 A | 11/2000 | Noda et al. |
| 6,149,670 A | 11/2000 | Worthen et al. |
| 6,149,677 A | 11/2000 | Dobak, III |
| 6,206,004 B1 | 3/2001 | Schmidt et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,245,095 B1 | 6/2001 | Dobak, III et al. |
| 6,251,129 B1 | 6/2001 | Dobak, III et al. |
| 6,254,626 B1 | 7/2001 | Dobak, III et al. |
| 6,261,312 B1 | 7/2001 | Dobak, III et al. |
| 6,264,680 B1 | 7/2001 | Ash |
| 6,287,326 B1 | 9/2001 | Pecor |
| 6,290,717 B1 | 9/2001 | Philips |
| 6,299,599 B1 | 10/2001 | Pham et al. |
| 6,312,452 B1 | 11/2001 | Dobak, III et al. |
| 6,338,727 B1 | 1/2002 | Noda et al. |
| 6,375,674 B1 | 4/2002 | Carson |
| 6,396,583 B1 | 5/2002 | Clare |
| 6,454,792 B1 | 9/2002 | Noda et al. |
| 6,530,945 B1 | 3/2003 | Noda et al. |
| 6,540,771 B2 | 4/2003 | Dobak, III et al. |
| 6,581,403 B2 * | 6/2003 | Whitebook et al. ........... 62/434 |
| 6,620,189 B1 | 9/2003 | Machold et al. |
| 6,673,098 B1 * | 1/2004 | Machold et al. ............... 607/96 |
| 6,676,688 B2 | 1/2004 | Dobak, III et al. |
| 6,692,518 B2 | 2/2004 | Carson |
| 6,786,916 B2 | 9/2004 | Noda et al. |
| 6,869,440 B2 | 3/2005 | Dobak, III |
| 7,241,307 B2 * | 7/2007 | Lennox ...................... 607/104 |
| 7,278,984 B2 | 10/2007 | Noda et al. |
| 7,287,398 B2 | 10/2007 | Noda et al. |
| 2002/0173834 A1 * | 11/2002 | Noda et al. ................. 607/105 |
| 2006/0122673 A1 * | 6/2006 | Callister et al. ............. 607/105 |

FOREIGN PATENT DOCUMENTS

| | | |
|---|---|---|
| WO | WO 00/09054 | 2/2000 |
| WO | WO 00/10494 | 3/2000 |
| WO | WO 00/38601 | 6/2000 |
| WO | WO 00/48670 | 8/2000 |
| WO | WO 00/66053 | 11/2000 |
| WO | 2004/006814 A2 | 1/2004 |
| WO | 2004/064622 A | 8/2004 |

OTHER PUBLICATIONS

Supplementary Partial European Search Report issued Oct. 29, 2009, pp. 1-5.

* cited by examiner

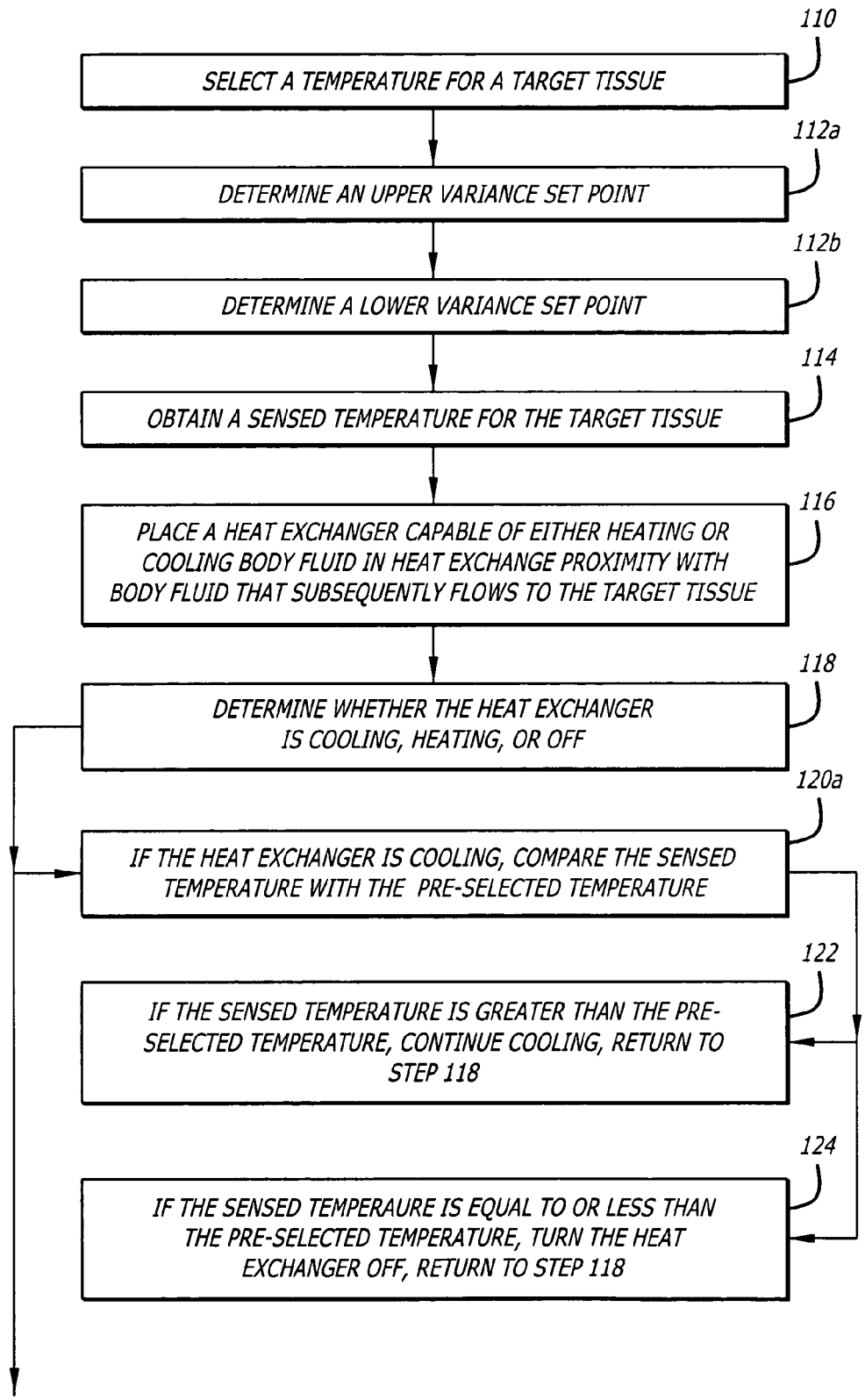

APPARATUS AND METHOD FOR PROVIDING ENHANCED HEAT TRANSFER FROM A BODY

RELATED APPLICATIONS

This application claims priority to U.S. Provisional Application Ser. Nos. 60/695,800 file Jun. 29, 2005 and 60/594,662 file Apr. 27, 2005, the entireties of which are hereby incorporated by reference.

FIELD OF THE INVENTION

The present invention relates generally to medical devices and methods and, more particularly, to a programmable, microprocessor based controller and method for controlling the temperature and flow of a thermal exchange fluid that is circulated through a heat exchange catheter inserted into a patient's body for the purpose of cooling or warming at least a portion of the patient's body.

BACKGROUND OF THE INVENTION

Under ordinary circumstances, the thermoregulatory mechanisms of a healthy human body serve to maintain the body at a constant temperature of about 37° C. (98.6° F.), a condition sometimes referred to as "normothermia." To maintain normothermnia, the thermoregulatory mechanisms act so that heat lost from the person's body is replaced by the same amount of heat generated by metabolic activity within the body. For various reasons such as extreme environmental exposure to a cold environment or loss of thermoregulatory ability as a result of disease or anesthesia, a person may develop a body temperature that is below normal, a condition known as "hypothermia." A person may develop a condition that is above normothermia, a condition known as "hyperthermia", as a result of extreme exposure to a hot environment, or malfunctioning thermoregulatory mechanisms, the latter being a condition sometimes called "malignant hyperthermia." The body may also establish a set point temperature (that is, the temperature which the body's thermoregulatory mechanisms function to maintain) that is above normothermia, a condition usually referred to as "fever." The present invention addresses these and other situations requiring alteration of at least a portion of a patient's body temperature.

Accidental hypothermia is generally a dangerous condition that may even be life threatening, and requires treatment. If severe, for example where the body temperature drops below 30° C., hypothermia may have serious consequences such as cardiac arrhythmias, inability of the blood to clot normally, or interference with normal metabolism. If the period of hypothermia is extensive, the patient may even experience impaired immune response and increased incidence of infection.

Simple methods for treating accidental hypothermia have been known since very early times. Such methods include wrapping the patient in blankets, administering warm fluids by mouth, and immersing the patient in a warm water bath. If the hypothermia is not too severe, these methods may be effective. However, wrapping a patient in a blanket depends on the ability of the patient's own body to generate heat to re-warm the body. Administering warm fluids by mouth relies on the patient's ability to swallow, and is limited in the temperature of the liquid consumed and the amount of fluid that may be administered in a limited period of time. Immersing a patient in warm water is often impractical, particularly if the patient is simultaneously undergoing surgery or some other medical procedure.

More recently, hypothermia may be treated in a more complex fashion. Heated warming blankets may be applied to a patient or warming lamps that apply heat to the skin of the patient may be used. Heat applied to the patient's skin, however, has to transmit through the skin by conduction or radiation which may be slow and inefficient, and the blood flow to the skin may be shut down by the body's thermoregulatory response, and thus, even if the skin is warmed, such mechanisms may be ineffective in providing heat to the core of the patient's body. When breathing gases are administered to a patient, for example a patient under anesthesia, the breathing gases may be warmed. This provides heat relatively fast to the patient, but the amount of heat that can be administered without injuring the patient's lungs is very limited. An alternative method of warming a hypothermic patient involves infusing a hot liquid into the patient via an IV infusion, but this is limited by the amount of liquid that can be infused and the temperature of the liquid.

In extreme situations, a very invasive method may be employed to control hypothermia. Shunts may be placed into the patient to direct blood from the patient through an external machine such as a cardiopulmonary bypass (CPB) machine which includes a heater. In this way, the blood may be removed from the patient, heated externally, and pumped back into the patient. Such extreme measures have obvious advantages as to effectiveness, but also obvious drawbacks as to invasiveness. The pumping of blood through an external circuit that treats the blood is generally quite damaging to the blood, and the procedure is only possible in a hospital setting with highly trained personnel operating the equipment.

Accidental hyperthermia may also result from various conditions. Where the normal thermoregulatory ability of the body is lost, because of disease or anesthesia, run-away hyperthermia, also known as malignant hyperthermia, may result. The body may also set a higher than normal set point resulting in fever which is a type of hyperthermia. Like hypothermia, accidental hyperthermia is a serious condition that may sometimes be harmful, even fatal. In particular, hyperthermia has been found to be neurodestructive, both in itself or in conjunction with other health problems such as traumatic brain injury or stroke, where a body temperature in excess of normal has been shown to result in dramatically worse outcomes, even death.

As with hypothermia, when the condition is not too severe, simple methods for treating the condition exist, such as cold water baths and cooling blankets, or antipyretic drugs such as aspirin or acetaminophen, and for the more extreme cases, more effective but complex and invasive means such as cooled breathing gases, cold infusions, and blood cooled during CPB also exist. These, however, are subject to the limitations and complications as described above in connection with hypothermia.

Although both hypothermia and hyperthermia may be harmful and require treatment in some case, in other cases hyperthermia, and especially hypothermia, may be therapeutic or otherwise advantageous, and therefore may be intentionally induced. For example, periods of cardiac arrest or cardiac insufficiency in heart surgery result in insufficient blood to the brain and spinal cord, and thus can produce brain damage or other nerve damage.

Hypothermia is recognized in the medical community as an accepted neuroprotectant and therefore a patient is often kept in a state of induced hypothermia. Hypothermia also has similar advantageous protective ability for treating or minimizing the adverse effects of certain neurological diseases or disorders such as head trauma, spinal trauma and hemorrhagic or ischemic stroke. Moreover, hypothermia has been found to be protective of the kidneys from damage due to exposure to nephrotoxic contrast media, such as is used during vasculature imaging methods like coronary angiography.

For the above reasons and others, it is sometimes desirable to induce whole-body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Hypothermia has also been found to be advantageous to protect cardiac muscle tissue after a myocardial infarct (MI).

Current methods of attempting to induce hypothermia generally involve constant surface cooling, by cooling blanket or by alcohol or ice water rubs. However, such cooling methods are extremely cumbersome, and generally ineffective to cool the body's core. The body's response to alcohol or ice water applied to the surface is to shut down the circulation of blood through the capillary beds, and to the surface of the body generally, and thus to prevent the cold surface from cooling the core. If the surface cooling works at all, it does so very slowly. There is also an inability to precisely control the temperature of the patient by this method. Patient safety issues may arise when, for example, ice water baths are used in the presence of defibrillators and other common hospital equipment.

If the patient is in a surgical setting, the patient may be anesthetized and cooled by cardiopulmonary bypass as described above. Generally, however, this is only available in the most extreme situations involving a full surgical team and full surgical suite, and importantly, is only available for a short period of time because of the damage to the blood caused by pumping the blood through the extracorporeal circuit comprised of pumps and tubing. Generally surgeons do not wish to pump the blood for periods longer than 4 hours, and in the case of stroke or traumatic brain damage, it may be desirable to induce hypothermia for longer than a full day. Because of the direct control of the temperature of a large amount of blood, this method allows fairly precise control of the patient's temperature. However, it is this very external manipulation of large amounts of the patient's blood that makes long term use of this procedure very undesirable.

Means for effectively adding or removing heat to or from the core of the body that do not involve pumping the blood with an external, mechanical pump have been suggested. For example, a method of treating hypothermia or hyperthermia by means of a heat exchange catheter placed in the bloodstream of a patient was described in U.S. Pat. No. 5,486,208 to Ginsburg, the complete disclosure of which is incorporated herein by reference. Means of controlling the temperature of a patient by controlling such a system is disclosed in U.S. Pat. No. 5,837,003, also to Ginsburg, the complete disclosure of which is incorporated herein by reference. A further system for such controlled intervascular temperature control is disclosed in U.S. Pat. No. 6,620,188 to Ginsburg et al., and U.S. Pat. No. 6,849,083 to Ginsburg, the complete disclosure of which is incorporated herein by reference. Those patents and publication disclose a method of treating or inducing hypothermia by inserting a heat exchange catheter having a heat exchange area including a balloon with heat exchange fins into the bloodstream of a patient, and circulating heat exchange fluid through the balloon while the balloon is in contact with the blood to add or remove heat from the bloodstream. (As used herein, a balloon is a structure that is readily inflated under pressure and collapsed under vacuum.)

A number of catheter systems for cooling tissue adjacent the catheter or regulating the temperature of the catheter using the temperature of fluid circulating within the catheter are shown in the published art. Some such catheters rely on a reservoir or similar tank for a supply of heat exchange fluid. For example, U.S. Pat. No. 3,425,419 to Dato, U.S. Pat. No. 5,423,811 to Imran et al., U.S. Pat. No. 5,733,319 to Neilson, et al., and U.S. Pat. No. 6,019,783 to Phillips, et al., disclose catheters with circulating heat exchange fluid from a tank or reservoir. For such systems that involve a catheter placed in the bloodstream, however, difficulties arise in sterilizing the fluid source between uses and rapidly changing the temperature of a large volume of fluid having a significant thermal mass.

It has been recognized that certain situations call for more cooling power than has been available using present systems. For example, it is postulated that reducing the time to cool a patient's blood immediately after a stroke or coronary event may improve the chance that the patient will recover, or at least reduce the amount of damage done due to ischemia. One way to reduce the time necessary to cool a patient's core body temperature to a desired target value is to maximize the cooling power available to remove heat from the patient's blood. However, presently available systems, such as those described above, are limited in the cooling power they can provide, or are too invasive as described in the case of heat exchange with extracorporeal circulation.

For the foregoing reasons, there is a need for a rapid and effective means to add or remove heat from the fluid supply for a catheter used to control the body temperature of a patient in an effective and efficient manner, while avoiding the inadequacies of the prior art methods. Such a system would rapidly, efficiently and controllably provide for heating or cooling the temperature of a patient or target tissue, and regulates the temperature of the patient or target tissue based on feedback from the temperature of the patient or target tissue. It would be particularly advantageous to provide a system that would reliably supply increased cooling power compared to present systems, provide for enhanced removal of heat from a patient's body, decrease the time necessary to reduce the patient's body temperature to a desired target temperature, and that may be deployed in both surgical and general wards of the hospital by at least one operator. The present invention fulfills this and other needs.

SUMMARY OF THE INVENTION

The present invention avoids many of the problems of the prior art by providing an improved system to control the heating and/or cooling of a catheter within a body. The system generally includes a control unit exterior to body, a number of conduits extending from the control unit, and a heat transfer catheter in communication with the control unit via the conduits. The control unit modulates the temperature of a heat transfer region on the catheter using an advantageous control methodology to avoid over-shooting a target temperature. The catheter and conduits preferably define a fluid circulation path, wherein the control unit modulates the temperature of the heat transfer region by adjusting the temperature of a heat transfer fluid within the circulation path. Desirably, the control unit defines a cavity and the conduits are connected to a cassette that fits within the cavity, the cassette having heat exchanger element through which the heat exchange fluid flows.

In one aspect of the present invention, a controller for controlling the temperature and flow of heat exchange fluid within a circuit is provided. The circuit is of a type that includes a heat exchange catheter, a heat exchanger, and a pump for flowing heat exchange fluid through the circuit. The controller includes a heat and/or cold generating element in thermal contact with the heat exchanger containing the heat exchange fluid. A patient sensor is positioned and configured to generate a signal representing a biophysical condition of the patient. The microprocessor in the controller receives the signal from the patient sensor and responds by controlling the generating element. The control unit further includes a mechanical drive unit for activating the pump contained in the circuit, and a safety sensor for detecting a fluid parameter in the circuit to generate a safety signal representative of the presence or absence of the fluid parameter. The safety signal is transmitted to the microprocessor that responds by controlling the operation of the pump. The sensor may be a bubble detector, and the fluid parameter is gas entrained in the heat exchange fluid. Alternatively, the circuit further comprises a reservoir, and the sensor is a fluid level detector for detecting a low fluid level in the reservoir.

In a still further aspect of the present invention, a heat transfer catheter flow system comprises a heat transfer medium circulation loop including a transfer catheter, a heat exchange element, and conduits coupled to the heat transfer catheter and heat exchange element that enable circulation of the heat transfer medium therebetween. The system further includes a pump head in contact with heat transfer medium within the circulation loop for circulating the medium through the loop. A cassette including the heat exchange element and the pump head mates with a controller housing a control circuit and a pump motor so that the pump head engages the pump motor. An electronic feedback loop that detects back-torque experienced by the pump motor provides feedback to a control circuit that in turn controls the speed of the pump motor.

In another aspect, the present invention provides a controller for controlling the temperature and flow of heat exchange fluid within a circuit of the type that has a heat exchange catheter, a heat exchange element, and a pump for flowing heat exchange fluid through the circuit. The controller includes a heat and/or cold generating element in thermal contact with the heat exchange element. A mechanical drive unit activates the pump contained in the circuit to pump the heat exchange fluid. The controller includes a microprocessor connected to control both the generating element and the mechanical drive unit. A safety system is provided for detecting problems in the circuit. The safety system includes a plurality of sensors that generate signals indicative of respective parameters of the system and/or patient. The signals are transmitted to the microprocessor that responds by controlling the operation of the generating element and the mechanical drive unit. In one embodiment, the safety system includes a sensor for detecting the fluid level within the circuit. In a further embodiment, the safety system includes a sensor for detecting the temperature of a location within the patient, and further may include a redundant sensor for detecting the temperature of a location within the patient wherein a microprocessor is responsive to a difference in the two sensed patient temperatures. Furthermore, the safety system may include sensors for detecting bubbles within the circuit, detecting the operating status of the generating element, or detecting the operating status of the mechanical drive unit.

The present invention also provides a method of regulating the temperature of patient, comprising the steps of: providing a heat exchange catheter system including a heat exchange catheter having a fluid path therethrough, a pair of conduits fluidly connected to the heat exchange catheter, and a heat exchanger connected via the conduits to circulate heat exchange medium through the exchange catheter; providing a first controller adapted to couple to the heat exchanger of the heat exchange catheter system, the first controller including a heat and/or cold generating element therein for exchanging heat at a first rate with the heat exchange medium within the heat exchanger; providing a second controller adapted to couple to the heat exchanger of the heat exchange catheter system, the second controller including a heat and/or cold generating element therein for exchanging heat at a second rate with the heat exchange medium within the heat exchanger; coupling the heat exchange catheter system with the first controller; inserting the heat exchange catheter into the patient; regulating the temperature of the patient by exchanging heat at the first rate between the generating element of the first controller and the heat exchanger; de-coupling the heat exchange catheter system from the first controller; coupling the heat exchange catheter system with the second controller; and regulating the temperature of the patient by exchanging heat at the second rate between the generating element of the second controller and the heat exchanger. The first and second controller may actually be the same physical device, but the method of coupling, decoupling, and subsequently recoupling the device may provide benefits, for example when the patient is being transported from one location to another, or is undergoing a therapeutic or diagnostic procedure, as described below.

The method may include performing a therapeutic or diagnostic procedure on the patient between the steps of decoupling the heat exchange catheter system from the first controller and the step of coupling the heat exchange catheter system with the second controller. Indeed, the first controller and the second controller may be the same physical device.

In a still further method of the present invention, the rate of change of a patient's body temperature is controlled using a heat transfer catheter and associated controller. The transfer catheter has a heat transfer region thereon, and the controller is placed in communication with the catheter via conduits. The controller is adapted to elevate or depress the temperature of the catheter heat transfer region relative to the body temperature. The patient's body temperature within a body cavity or in another location is sensed, while the temperature of the heat transfer region is determined. A target temperature is then selected. The target temperature may be different than the body temperature, or may be the same if maintenance of normal patient temperature is the goal. A ramp rate equal to the time rate of change of temperature from the body temperature to the target temperature is selected. The temperature of the transfer region of the catheter based on the ramp rate is set. The method includes monitoring the temperature differential between the target temperature and the body temperature, and reducing the ramp rate when the temperature differential reduces below a predetermined threshold. Desirably, the heat transfer catheter and conduits defined a fluid circulation path therethrough, wherein the step of setting the temperature of the catheter heat transfer region comprises setting the temperature of a circulating fluid within the circulation path. Preferably, the step of determining the temperature of the catheter heat transfer region comprises directly or indirectly sensing the temperature of the circulating fluid. A comparison may be made between the target temperature and the temperature of the circulating fluid, which is then used to adjust the temperature of the circulating fluid.

In a further aspect, the present invention provides a system capable of reducing the temperature of a patient in a controllable and rapid matter. The system includes an arrangement of heat exchangers, pumps and cooling media that is capable of removing sufficient heat energy so as to be able to maintain the temperature of a primary coolant loop in the range of 0-5 degrees centigrade, even when heat loads are in the range of about 400 to about 550 watts.

In yet another aspect, the present invention includes a system for adjusting the temperature of a patient, comprising: a primary fluid circuit, the circuit including a primary fluid reservoir, a primary fluid circuit pump, a heater cooler, primary fluid circuit lines connecting the primary fluid circuit pump to the primary fluid reservoir to the heater/cooler such that a continuous flow path for circulating primary fluid from the reservoir to the heater/cooler and back to the primary fluid reservoir is formed; access points in the primary fluid circuit, the access points fluidly connecting the primary fluid circuit to a primary fluid circuit side of a heat exchanger, the heat exchanger also having a secondary fluid circuit side; a heat exchange catheter insertable within a patient, the catheter configured to increase, decrease or maintain the temperature of the patient; a secondary fluid circuit for flowing secondary fluid through the secondary circuit side of the heat exchanger and the heat exchange catheter, the secondary fluid circuit including a secondary fluid reservoir, and a secondary fluid circuit pump for flowing a secondary heat exchange fluid from the secondary fluid reservoir through secondary fluid circuit to the heat exchange catheter and back through the secondary fluid circuit to the secondary fluid reservoir; at least one fluid sensor configured to provide a signal representative of a temperature of the primary or secondary fluid circuit; a patient sensor configured to provide a signal representative of a temperature of the patient; and a controller configured to receive the signals from the patient sensor and the primary fluid sensor and being responsive to the signals to control the heater/cooler to adjust the temperature of the fluid flowing within the fluid circuits. In yet another aspect, the volume of the primary fluid pathway or circuit increases when the heat exchanger is connected with the primary fluid pathway or circuit.

In a further aspect, the present invention includes the case wherein the controller includes a microprocessor configured to be responsive to sensors and to provide control signals as needed to control the operation of the system.

In a still further aspect, the present invention includes a power supply for supplying power to the system, including the heater/cooler; controller circuitry for controlling the operation of the system, the controller circuitry including means for determining if the power supply is operative and operating within parameters determined to be appropriate, means for monitoring the operation of the system, means for determining an error state of the monitored system, and means for alerting an operator of the presence of an error state.

In yet another aspect, the present invention includes the cases wherein the controller controls the heater/cooler to drive the temperature of the fluid in the primary fluid circuit towards a predetermined temperature prior to fluidly connecting the heat exchanger to the primary fluid circuit and wherein the controller controls the heater/cooler to drive the temperature of the fluid in the primary fluid circuit towards a predetermined temperature prior to initiation of treatment of a patient.

In a still further aspect of the present invention, the primary fluid circuit includes temperature sensors disposed in the primary fluid circuit, the temperature sensors providing signals representative of the temperature of the primary fluid passing through the access points flowing into and out of the primary fluid circuit side of the heat exchanger. Alternatively, the temperature difference between the fluid flowing into and out of the primary fluid circuit side of the heat exchanger is proportional to the heat exchange being delivered to the secondary fluid circuit, and is representative of the heat exchange being delivered to the patient. In yet another alternative aspect, the controller is responsive to the signals provided by the temperature sensors to determine the difference in the temperature of the primary fluid flowing into and out of the access points, and to provide an alert if the determined difference is indicative of a problem condition, or the controller is responsive to the signals provided by the temperature sensors to provide an alert if the signals are indicative of a problem condition.

In another aspect of the present invention, the secondary fluid reservoir includes an air trap disposed between an inlet to the reservoir and the secondary fluid circuit pump. In one aspect the air trap is a semi-permeable member permitting at least a portion of the secondary fluid to flow through the semi-permeable member and in another aspect the air trap is formed from foam.

In yet another aspect of the present invention, the secondary fluid circuit contains a particulate filter. In one aspect, the particulate filter is a semi-permeable member permitting at least a portion of the secondary fluid to flow through the semi-permeable member and in another aspect the particulate filter is formed from foam for formed from a screen.

In a further aspect, the present invention also includes a level detector disposed in the secondary fluid circuit to detect a level of the fluid within the secondary fluid circuit, the level detector providing a signal representative of the level of fluid in the secondary fluid circuit to the controller. In one aspect, the level detector is disposed in cooperation with the secondary fluid reservoir to detect a level of the fluid within the secondary fluid reservoir.

In yet another aspect of the present invention, the level detector may be a bubble detector or an air in line detector.

In yet another aspect of the present invention, the controller sends a start signal to the secondary fluid pump in response to a signal from the level detector representative of a predetermined fluid level. Alternatively, the controller may send a stop signal to the secondary fluid pump in response to a signal from the level detector representative of a predetermined low fluid level.

In one aspect of the present invention, the secondary fluid circuit pump and secondary fluid reservoir and heat exchanger are included in a cassette configuration that is provided to the operator in a sterile condition. In a further aspect, the present invention also includes a reusable housing in which are disposed the primary fluid reservoir, primary fluid circuit pump, microprocessor and a secondary fluid circuit pump motor, the housing being configured to removably receive the cassette such that the secondary fluid circuit pump releasably engages the secondary fluid circuit pump motor.

In yet another aspect of the present invention, the access points include releasable couplers for releasably coupling the heat exchanger to the primary fluid circuit. In one aspect, the releasable couplers fluidly seal when not connected to the primary fluid circuit to minimize primary fluid loss from the primary fluid circuit side of the heat exchanger and the primary fluid circuit.

In another aspect, the present invention includes a quick connect coupler configured to allow electrical connection of a sensor line to a controller at about the same time the releasable couplers of the heat exchanger are engaged. This provides for easier and more rapid setup of the heat exchanger, which is advantageous during an emergency situation. This arrangement also prevents errors that may occur if a caregiver neglects to connect the sensor line before start up of the system.

In still another aspect of the present invention, the primary fluid circuit further comprises a check valve for controlling a fluid pressure within the primary fluid circuit such that the fluid pressure does not exceed a predetermined value. In yet another aspect, the cassette and catheter may be disconnected from the primary fluid circuit and connected to a different primary circuit without compromising sterility or fluid isolation of the secondary fluid circuit of the cassette and catheter.

In another aspect of the present invention, the fan/blower output of the heater/cooler is reduced when the controller determines that a sensed temperature is within a predetermined range. In another aspect, the fan/blower output of the heater/cooler is reduced when the controller determines that the sensed temperature is within a predetermined range for a predetermined amount of time. In still another aspect, an output of the primary and/or secondary fluid pump is reduced when the controller determines that a sensed temperature is within a predetermined range. In a still further aspect, the output of the primary and/or secondary pump is reduced when the controller determines that demand for patient temperature change is reduced.

In yet another aspect of the present invention, the primary fluid circuit is configured such that the majority of volume of primary fluid contained with the heat exchanger is recovered to the primary fluid reservoir prior to disconnection of the heat exchanger from the primary fluid circuit.

In another aspect of the present invention, the heat exchanger is provided to the operator with the primary fluid side pre-filled with primary fluid. In still another aspect, the heat exchanger is provided to the operator with the secondary fluid side pre-filled with secondary fluid.

In one aspect of the present invention the heat exchanger when connected is maintained in electrical isolation from the heater/cooler and electrical inputs to components of the primary fluid loop.

In another aspect of the present invention, the primary fluid circuit includes a means for maintaining the electrical conductivity at a value below a predetermined value. In another aspect of the present invention, the means includes a sensor configured to sense an electrical characteristic of the fluid within the fluid circuit.

In still another aspect, the present invention includes a priming fluid circuit for providing secondary heat exchange fluid to the secondary fluid circuit. In a further aspect, the priming fluid circuit includes a prime line and a vent line, at least of one of the prime line and vent line having a valve, and at least one sensor for determining when the secondary circuit is sufficiently filled with fluid. In a further aspect, at least one of the valves in the prime line and vent line is a clamp that engages the line to obstruct fluid flow in the line. In yet another aspect, the at least one of the valves in the prime line and vent line are controlled by the controller to initiate and complete filling the secondary fluid circuit with secondary fluid.

In another aspect of the present invention, the access points are configured to receive primary circuit fluid to fill the primary fluid reservoir. Still further, at least one of the fluid lines is engaged with the at least one of the fluid lines of the cassette when the cassette is removably received by the housing.

In still another aspect of the present invention, the controller controls the temperature of the primary fluid circuit at a level sufficient to prevent freezing of the secondary fluid in the secondary fluid circuit.

In yet another aspect of the present invention the, heat exchanger includes a pair of intermediate fluid pathways. The two intermediate pathways, a primary intermediate pathway and a secondary intermediate fluid pathway, are physically separated from each other, but are in thermal communication with each other. This provides for the exchange of heat energy between the intermediate fluid pathways, while preventing the possibility of contaminating the secondary heat exchange fluid which may flow into a patient with primary circuit fluid, which may or may not be biocompatible. In a further aspect, the physical separation of the intermediate fluid pathways ensures that the primary fluid circuit will not be contaminated should the secondary fluid circuit be invaded by blood or other bodily fluids. In still another aspect, the intermediate fluid pathways, when connected to their respective primary or secondary fluid circuits, increase the volume of these circuits.

Other features and advantages of the invention will become apparent from the following detailed description, taken in conjunction with the accompanying drawings, which illustrate, by way of example, the features of the invention.

DETAILED DESCRIPTION OF THE INVENTION

Figure 1:
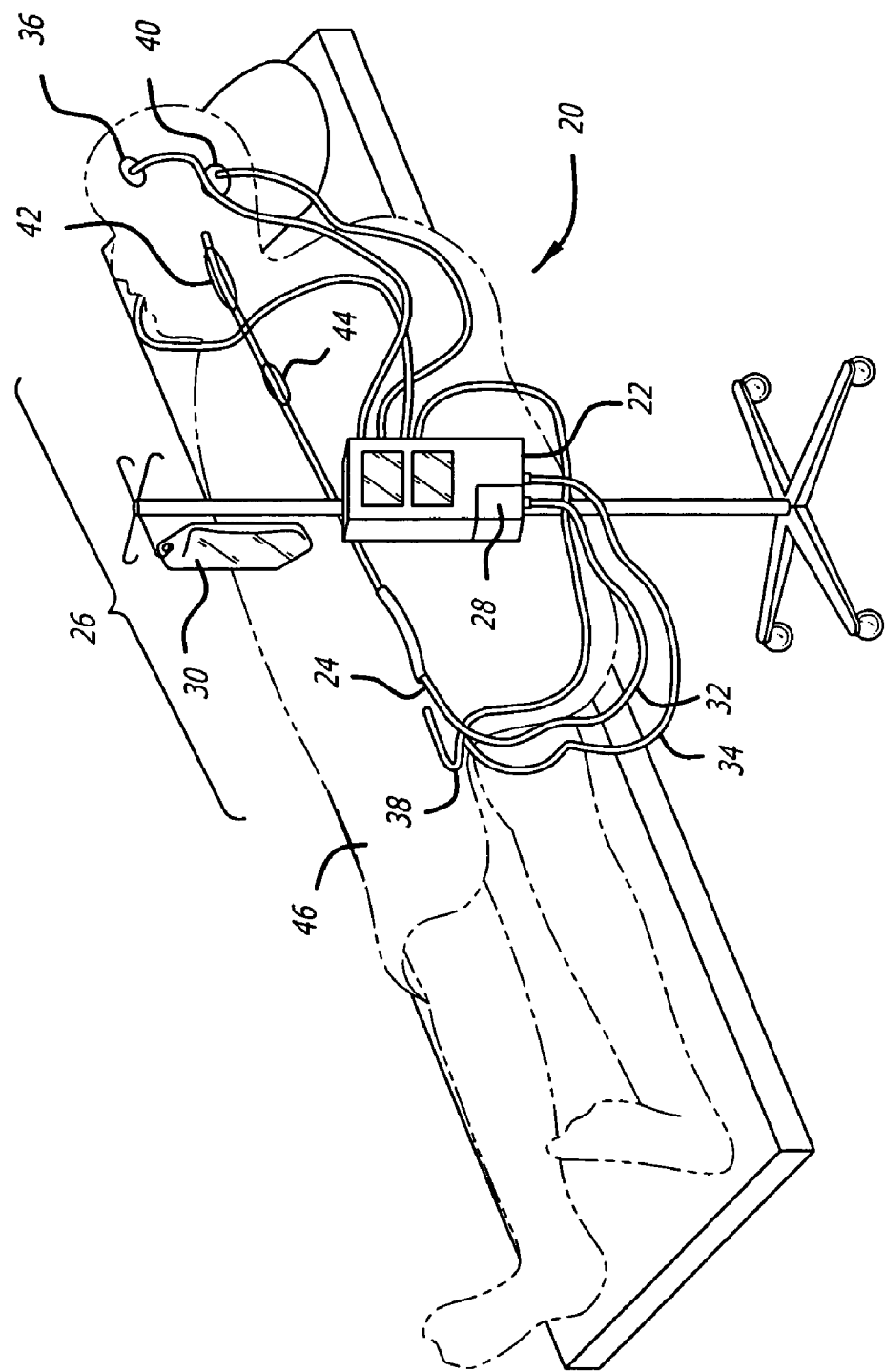
FIG. 1 is a perspective view of a patient undergoing treatment using a system in accordance with the present invention.

The present invention is primarily intended to include a catheter placed in the bloodstream of a patient for regulating the patient's body temperature, although those of skill in the art will understand that various other applications for the system of the present invention are possible. Indeed, the present invention may have applications beyond controlling the temperature of an internal body fluid, and the claims should not be so limited. In a preferred application, one or more of the heat exchange catheters of the present invention are positioned within a patient's vasculature to exchange heat with the blood in order to regulate the overall body temperature, or to regulate the temperature of a localized region of the patient's body. Heat exchange fluid is then circulated through the catheter to exchange heat between the blood and the heat exchange fluid, and a controller manages the functioning of the system. The catheters may be, for example, suitable for exchanging heat with arterial blood flowing toward the brain to cool the brain, and may thus prevent damage to brain tissue that might otherwise result from a stroke or other injury, or cooling venous blood flowing toward the heart to cool the myocardium to prevent tissue injury that might otherwise occur following an MI or other similar event.

In general, the invention provides a preferred control unit and method for controlling the temperature and flow of heat transfer fluid for a heat transfer catheter used for controlling the body temperature of a patient. The control unit initially automatically supplies heat transfer fluid to the heat transfer catheter to prime the heat exchange catheter for use. It also receives input from the user, receives temperature information from sensors that sense patient temperature information, and based thereon, automatically controls the temperature and flow of the heat transfer fluid. Further, based on feedback from a pump in a cassette containing the heat transfer fluid, the control unit supplies heat transfer fluid at a relatively constant pressure. The cassette and the controller, working together, have several warning or alarm states that alert the user of potentially hazardous situations, for example, by shutting down the pump motor and notifying the user if the fluid level in the cassette is unacceptably low.

Overview of Heat Exchange System

Any suitable heat exchange catheter may be utilized in a heat exchange system for regulating the temperature of a patient or a region of the patient's body and controlled by the control unit as disclosed herein. In addition to the catheters disclosed herein, and by way of illustration and not of limitation, catheters that may be utilized in this invention are the catheters disclosed in U.S. Pat. No. 5,486,208 to Ginsburg, U.S. Pat. No. 5,837,003 to Ginsburg, U.S. Pat. No. 6,610,083 to Keller et al., U.S. Pat. No. 6,702,840 to Keller et al., U.S. Pat. No. 6,752,786 to Callister, U.S. Pat. No. 6,620,188 to Ginsburg et al., U.S. Pat. No. 6,849,083 to Ginsburg, U.S. Pat. No. 5,624,392 to Saab, and U.S. Pat. No. 6,440,158 to Saab, the complete disclosure of each of which is hereby incorporated in full herein by reference. It will be understood by those skilled in the art that for the purposes of providing heat exchange with a patient at the rates possible using the various embodiments of the present invention, a catheter with sufficient heat exchange power must be employed.

While the various embodiments of the system and method of the present invention will be described with reference to providing a source of cooling or heating fluid for circulation within a catheter, those skilled in the art will understand that the fluid may also be circulated through other devices designed to alter the temperature of a patient. For example, instead of a catheter, the fluid may be circulated through a heating or cooling pad or blanket designed to be used externally to a patient.

One example of such a heat exchange catheter system 20 is shown in FIG. 1, and includes a control unit 22 and a heat exchange catheter 24 formed with at least one heat transfer section 44. The heat transfer section or sections are located on that portion of the catheter 24, as illustrated by section 26, that is inserted into the patient. This insertion portion is less than the full-length of the catheter and extends from the location on the catheter just inside the patient, when the catheter is fully inserted, to the distal end of the catheter. The control unit 22 may include a fluid pump 28 for circulating a heat exchange fluid or medium within the catheter 24, and a heat exchanger component for heating and/or cooling circulating fluids within the heat transfer system 20. A reservoir or fluid bag 30 may be connected to the control unit 22 to provide a source of heat transfer fluid such as, saline, blood substitute solution, or other biocompatible fluid. A circulatory heat exchange flow channel within the catheter may be respectively connected to inlet 32 and outlet 34 conduits of the pump 28 for circulation of the heat transfer fluid through the balloon to cool the flow of body fluid such as blood within a selected body region. A similar arrangement may be implemented for heating of selected body regions simultaneously or independently of each other using the cooling component of the system.

The control unit 22 may further receive data from a variety of sensors which may be, for example, solid-state thermocouples to provide feedback from the catheter and various sensors to provide patient temperature information representing core temperature or temperature of selected organs or portions of the body. For instance, sensors may include a temperature probe 36 for the brain or head region, a rectal temperature probe 38, an ear temperature probe 40, an esophageal temperature probe (not shown), a bladder temperature probe (not shown), and the like. Alternatively, a temperature probe may be placed in a patient's blood vessel at a location adjacent the heat transfer balloon. In yet another embodiment, the temperature probe may be placed in the blood stream distal of the heat transfer balloon.

Based upon sensed temperatures and conditions, the control unit 22 may direct the heating or cooling of the catheter in response. The control unit 22 may activate a heat exchanger at a first sensed temperature to heat fluid which is then circulated through the balloon, and may also de-activate the heat exchanger at a second sensed temperature which may be relatively higher or lower than the first sensed temperature or any other predetermined temperature. Alternatively, the control unit may actively cool the heat exchange fluid to cool the balloon. The control unit 22 may operate multiple heat transfer units to independently heat or cool different selected heat transfer sections to attain desired or preselected temperatures in body regions. Likewise, the controller 22 may activate more than one heat exchanger to control temperature at particular regions of the patient's body. The controller might also activate or de-activate other apparatus, for example external heating blankets or the like, in response to sensed temperatures.

The regulation exercised over the heat transfer catheters or other devices may be a simple on-off control, or may be a significantly more sophisticated control scheme including regulating the degree of heating or cooling, ramp rates of heating or cooling, proportional/integral/derivative (PID) or nonlinear control as the temperature of the heat exchange region or patient approaches a target temperature, or the like.

The control unit 22 may further include a thermoelectric cooler and heater (and associated flow conduits) that are selectively activated to perform both heating and cooling functions with the same or different heat transfer mediums within the closed-loop catheter system. For example, a first heat transfer section 42 located on the insertion portion 26 of at least one temperature regulating catheter 24 may circulate a cold solution in the immediate head region, or alternatively, within a carotid artery or other blood vessel leading to the brain. The head temperature may be locally monitored with temperature sensors 36 positioned in a relatively proximate exterior surface of the patient or within selected body regions. Another heat transfer section 44 of the catheter 24 also located on the insertion portion 26 may circulate a heated solution within a collapsible balloon or otherwise provide heat to other body locations through heat elements or other mechanisms described in accordance with other aspects of the invention. While heat exchange catheter 24 may provide regional hypothermia to the brain region for neuroprotective benefits, other parts of the body may be kept relatively warm so that adverse side effects such as discomfort, shivering, blood coagulopathies, immune deficiencies, and the like, may be avoided or minimized. Warming of the body generally below the neck may be further achieved by insulating or wrapping the lower body in a heating pad or blanket 46 while the head region above the neck is cool. It should be understood of course that multiple heat exchange sections of the catheter 24 may be modified to provide whole body cooling or warming to affect body core temperature.

Exemplary Heat Exchange System

The present invention contemplates the use of a re-usable controller or control console having a heater/cooler device therein and which receives a disposable heat exchange element coupled via conduits to a distal in-dwelling heat exchange catheter. More specifically, the controller desirably includes an outer housing having an opening or slot for receiving the heat exchange element, the opening and housing ensuring reliable positioning of the heat exchange element in proximity with the heater/cooler device. In this manner, set up of the system is facilitated because the operator only needs to fully insert and seat the heat exchange element into the controller opening in order to couple the reusable and disposable portions of the system.

Figure 2:
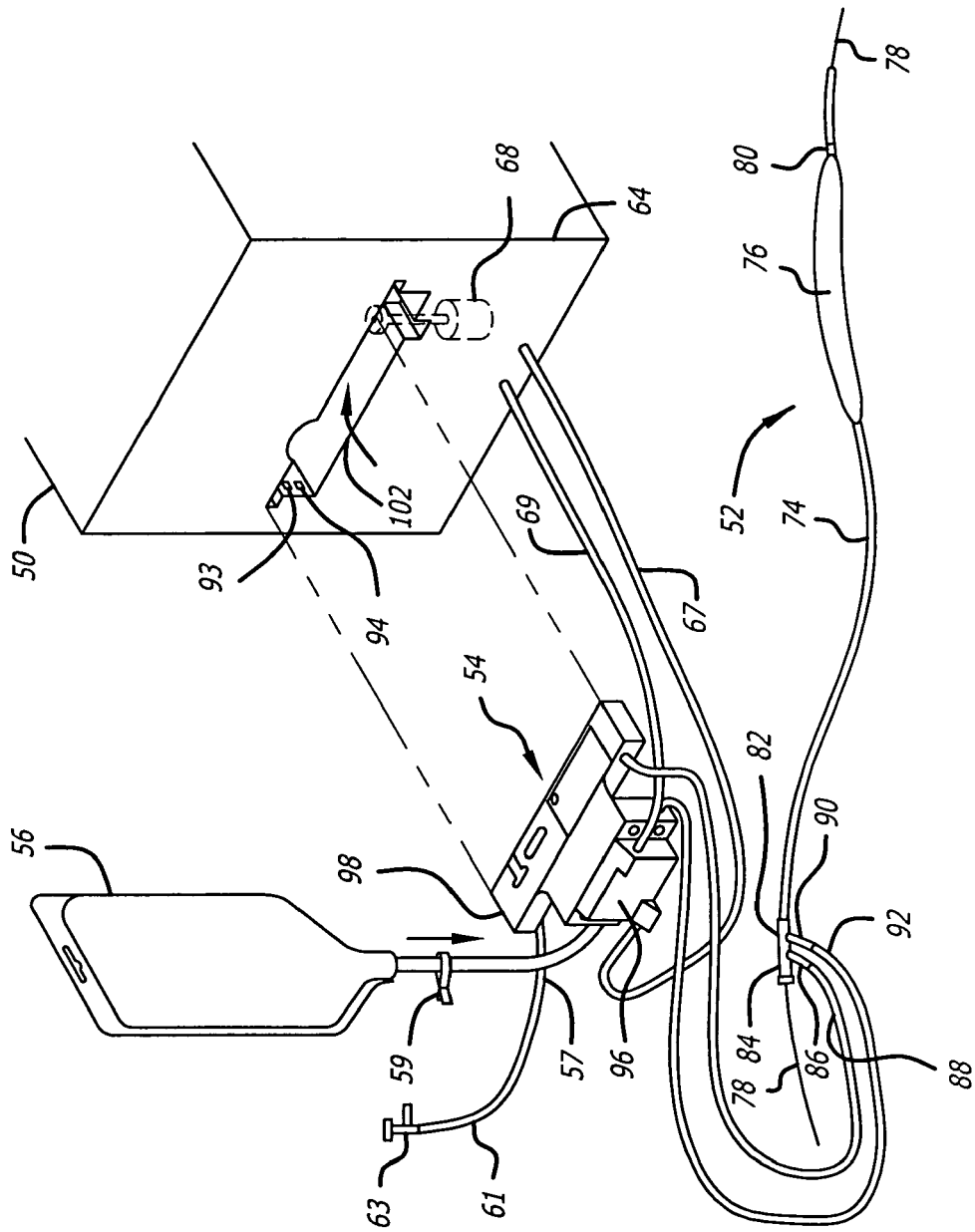
FIG. 2 is a schematic illustration of a disposable heat exchange cassette attached to a heat exchange catheter and an external fluid source, and positioned for insertion into a suitable opening in a re-usable control unit of the present invention, FIGS. 3A-3B together show a flowchart of a control scheme of the heat exchange system of the present invention.

In an exemplary embodiment, FIG. 2 illustrates a heat exchange catheter system that includes a re-usable control unit 50 and a plurality of disposable components including a heat exchange catheter 52, a heat exchange cassette 54, a saline bag 56, and a plurality of fluid flow conduits including a two-way conduit 74 extending distally from the heat exchange cassette 54. The re-usable control unit 50 includes an outer housing 64 within which is provided a heater/cooler, a primary fluid circuit reservoir, a primary fluid circuit pump, a controller processor and various control cables and temperature, pump and flow controls, all not shown. Within control unit 50 is also a pump drive motor 68 which drives a secondary fluid circuit pump disposed within heat exchange cassette 54 through a solenoid driven engagement swing arm and coupling (not shown), an optical beam source 93 and optical beam sensor 94 which may be used to determine a fluid level within the heat exchange cassette 54. In addition, a manual input unit (not shown) utilizing a graphical user interface enables an operator to enter desirable operating parameters of the controller, for example a preselected temperature for the brain. Each of the electronic devices provided within the control unit 50 communicate through suitable wiring. The heat exchange cassette 54 is in fluid communication with the primary fluid circuit through primary circuit fluid conduits or access points 67, 69, thus forming a closed fluid circuit comprising the primary fluid circuit reservoir, primary fluid circuit pump and heat exchange cassette 54.

The heat exchange catheter 52 is formed with a catheter conduit 74 and a heat exchanger 76 which may be, for example, a heat exchange balloon operated using a closed-loop flow of a biocompatible fluid that serves as the heat exchange medium. The catheter 52 may include a working lumen (not shown) for injection of drugs, fluoroscopic dye, or the like, and for receipt of a guidewire 78 for use in placing the catheter at an appropriate location in the patient's body. A sensor 80 may be provided on the catheter 52 distal to the heat exchanger 76 to monitor the temperature of the heat exchange balloon, and other sensors (not shown) may be provided as desired to monitor the blood temperature at the distal tip of the catheter, at the proximal tip of the balloon, or at any other desired location along the catheter.

The heat exchange cassette 54 includes a heat exchanger 96 and a fluid reservoir compartment that houses a secondary fluid circuit pump. In a preferred embodiment, the secondary fluid circuit is a closed system physically isolated from the primary fluid circuit by heat exchanger 96 but with the secondary fluid circuit and the primary fluid circuit in heat exchange communication through the heat exchanger. This arrangement is advantageous in that different fluids may be used in the primary fluid circuit that are not necessarily biocompatible so as to maximize the efficiency of the heat exchanger 96 during heating or cooling of a patient.

As seen in FIG. 2, the proximal end of the catheter conduit 74 may be connected to a multi-arm adapter 82 for providing separate access to various channels in the catheter 52. For example, a first arm 84 may provide access to the working lumen of the catheter 52 for insertion of the guidewire 78 to steer the heat exchange catheter to the desired location. First arm 84 may also be used to provide access to the blood stream for a temperature probe to monitor the blood temperature for control input.

Where the heat exchanger 76 is a heat exchange balloon for closed-loop flow of secondary fluid, the adapter 82 may contain a second arm 86 connected to an inflow line 88, and a third arm 90 connected to an outflow line 92. The inflow line 88 and outflow line 92 are therefore placed in flow communication with respective inflow and outflow channels (not shown) provided in the conduit 74 and heat exchanger 96. In this regard, the inflow and outflow lines 88, 92 may come together to form the dual channel conduit 62 connected to the heat exchange cassette 54.

A vent tube 61 including a valve 63 may be used to assist in priming the secondary fluid circuit. Furthermore, an external biocompatible fluid source such as the saline bag 56 may be placed in fluid communication with the secondary fluid circuit using suitable connecters. As will be explained further below, the external fluid source 56 is used to prime the secondary fluid circuit, including the closed-loop heat exchange balloon system.

Still with reference to FIG. 2, and as described above, the heat exchange cassette 54 depicted in this embodiment desirably includes the heat exchanger 96 and a fluid reservoir compartment 98, which also holds the secondary fluid pump. The secondary fluid circuit pump in the reservoir compartment 98 pumps heat exchange fluid through the secondary fluid circuit through the heat exchanger 96, and through the associated conduits and catheter 52. As mentioned, the heat exchange cassette 54 is configured to install into the control unit 50. In this regard, the heat exchange cassette 54 is desirably sized to fit through an elongate slot 102 in the control unit housing 64. Once inserted, the cassette 54 is placed in proximity to and engaged with the pump drive motor 68. The heat exchanger 96 is connected to the primary fluid circuit using inflow and outflow conduits, or access points, 67, 69.

When the heat exchanger cassette 54 is properly installed in the control unit 50, the heater/cooler may act to heat or cool the primary heat exchange fluid as that fluid is circulated through in heat exchange contact with the secondary fluid in heat exchanger 96. The secondary fluid, which is either being heated, cooled or maintained by the heat exchange contact with the primary fluid in the heat exchanger 96, is pumped through the conduits leading to the in-dwelling heat exchanger 76. When the heat exchange fluid is circulated through the heat exchanger 76 located in the patient's body, it may act to add or remove heat from the body. In this way, the control unit 50 regulates the blood temperature of the patient as desired.

A solid-state thermoelectric heater/cooler may be used to heat or cool the primary circuit fluid, and such use is advantageous because the same unit is capable of either generating heat or removing heat by simply changing the polarity of the current activating the unit. Therefore, the heater/cooler may be conveniently controlled so as to supply or remove heat from the system without the need for two separate units and without exchange of the heat exchange cassette or catheter. In another embodiment, a variable speed vapor compressor/heat pump could also be used as the heater/cooler. Alternatively, a resistive heater could be used in combination with a variable or constant speed compressive cooler.

The heater/cooler and the pump drive motor 68 are responsive to the controller processor, which receives data input through electrical connections to numerous sensors, for example body temperature sensors positioned to sense the temperature at various locations within the patient. For example, the temperature may be sensed at the patient's ear, brain region, bladder, rectum, esophagus, or other appropriate location as desired by the operator. Also, as mentioned, a sensor 80 may monitor the temperature at a location distal of the heat exchanger 76, and other sensors along the catheter 52 may provide input to the controller processor. Additionally, the manual input unit allows an operator to provide operating parameters to the control system such as, for example, a pre-selected temperature for the brain and/or the whole body of the patient. The operator input parameters are communicated to the controller processor by means of appropriate wiring.

The controller processor coordinates the various data received and selectively actuates the several operational subsystems to achieve and maintain desired results; i.e., proper regulation of the patient's body temperature. For example, the processor may actuate the heater/cooler to increase the amount of heat it is removing if the actual temperature is above the specified temperature, or it may decrease the amount of heat being removed if the temperature is below the specified temperature. Alternatively, the processor may slow or stop the pumping of the primary or secondary, or both, heat exchange fluids when the sensed body or regional temperature reaches the desired temperature.

In operation, the heater/cooler warms or chills the fluid in the primary fluid circuit in response to temperature signals received from the temperature sensors described above to alter the temperature of the patient's body, or a portion of the patient's body, as desired. The changes in temperature of the primary fluid circuit is transferred to the fluid circulating in the secondary fluid circuit using the heat exchanger 96, in a manner that is well known to those skilled in the art. Thus, the heater/cooler is used to indirectly affect the temperature of the patient, or a portion of the patient by heating or cooling the fluid circulating in the secondary fluid circuit.

Referring still to FIG. 2, the heat exchange cassette 54 of this embodiment is shown as being attached to a heat exchange catheter 52, external fluid source 56 is positioned in cooperation with a suitable reusable control unit 50. Prior to commencing treatment, the heat-exchange unit 54 is inserted into the reusable control unit 50, the external fluid source 56 is attached to the fill port and the pump 68 is automatically or passively primed and the disposable system filled, after which the catheter is ready for insertion in-the vasculature of the patient, for example in the inferior vena cava or the carotid artery. Chilled or warmed biocompatible fluid such as, for example, saline filling the secondary circuit, is pumped into the closed circuit catheter, which exchanges heat directly with the patient's blood. The control unit serves to automatically-control the patient's temperature. Once treatment with the catheter is complete, the catheter is removed from the patient and the cassette is removed from the reusable control unit. Both the catheter and cassette may then be discarded. The reusable control unit, however, which never comes into direct contact with the secondary heat exchange fluid, is ready for immediate use for treatment on other patients, along with a new cassette and catheter and fresh external fluid source. Alternatively, the heat exchanger 96 may be separated from the cassette 54, cleaned and sterilized, while the cassette is discarded. In yet a further alternative, the entire heat exchange cassette 54 may be suitably reconditioned for use with another patient.

Exemplary Method of Temperature Control

Figure 3B:
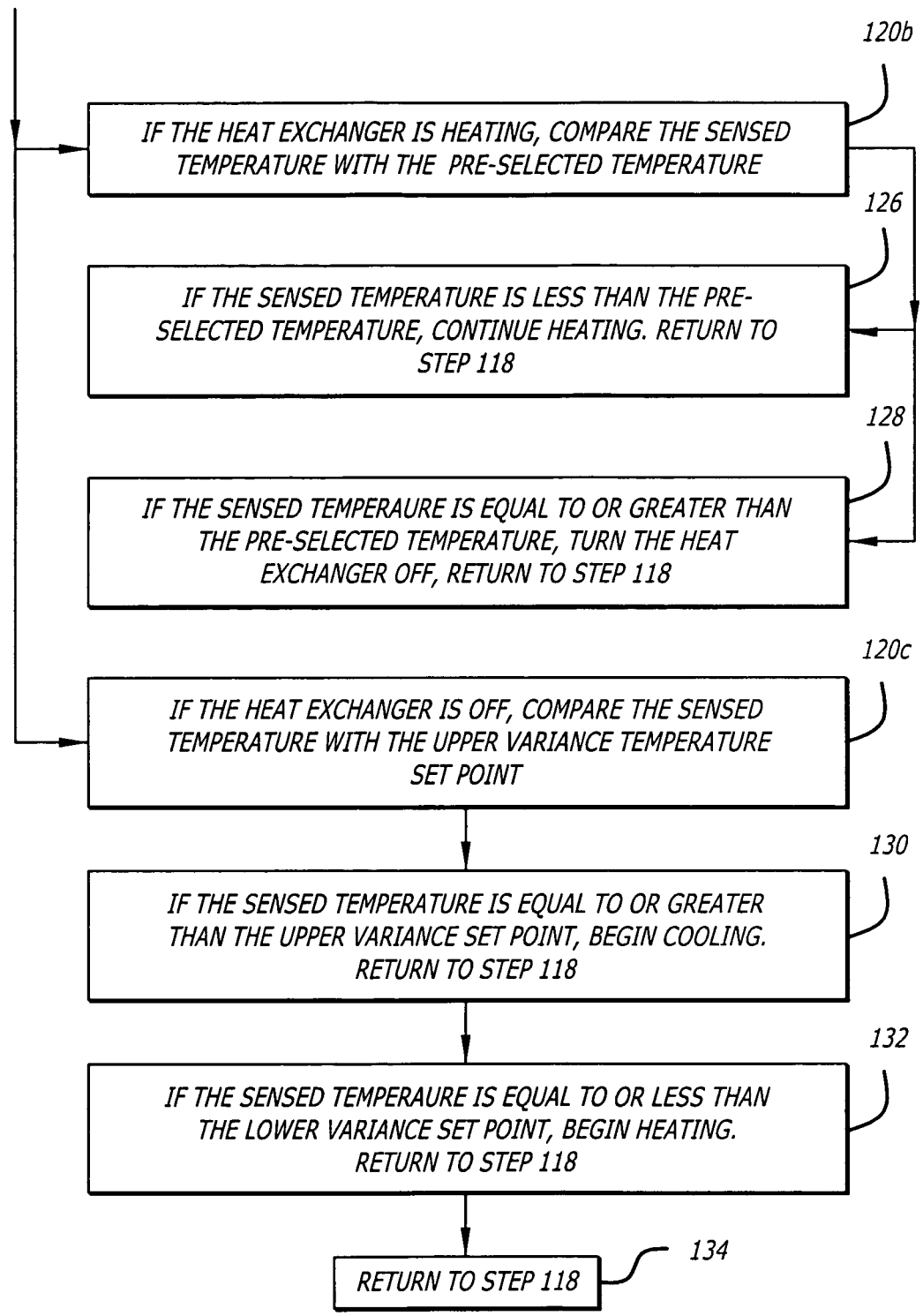

The flowchart seen in FIGS. 3A and 3B illustrates an exemplary sequence of steps that the controller processor of the system coordinates during temperature regulation of a patient. First, in step 110, a target temperature for the target tissue (which may be the entire body) is selected, generally by user input. The target temperature may be different than the body temperature, or may be the same if maintenance of normal patient temperature is the goal. Steps 112a and 112b involve determination of an upper variance set point and a lower variance set point, respectively. This is generally a pre-set buffer range above and below the target temperature that is built or programmed into the controller processor. These variance set points straddle the target temperature and create a buffer range of temperature within which the controller operates.

More specifically, the sensed temperature for the target tissue is obtained in step 114 prior to or after step 116 in which a heat exchanger capable of either heating or cooling body fluid is placed in proximity with body fluid that subsequently flows to the target tissue. Based on user input, or on a comparison between the target temperature and the sensed tissue temperature, a determination is made in step 118 as to whether the heat exchanger will be operating a cooling mode, a heat mode, or a maintaining mode. That is, if the target temperature equals the tissue temperature then there will be no need to initially heat or cool the body fluid and the control unit will control the heat exchanger to maintain the tissue or blood temperature at the target temperature.

The determination step 118 leads to three different modes of operation of the system, depending on whether the system will be COOLING, HEATING, or OFF. These modes of operation correspond to steps 120a, 120b, and 120c, which appear on both the FIGS. 3A and 3B.

If the system is in the COOLING mode, the flowchart logic leads to step 120a which compares the sensed tissue temperature with the pre-selected target temperature. If the tissue temperature is greater than the target temperature, the system continues cooling as indicated in step 122, and the processor returns to decision step 118. On the other hand, if the sensed tissue temperature is equal to or less than the target temperature, the heat exchanger is converted to the OFF mode as indicated in step 124 and the processor returns to decision step 118.

If the system is in the HEATING mode, the flowchart logic leads to step 120b which also compares the sensed tissue temperature with the pre-selected target temperature. If the tissue temperature is less than the target temperature, the system continues heating as indicated in step 126, and the processor returns to decision step 118. On the other hand, if the tissue temperature is equal to or greater than the target temperature, the heat exchanger is converted to the OFF mode as indicated in step 128, and the processor returns to decision step 118.

If the system is in the OFF mode, the flowchart logic leads to step 120c which compares the sensed tissue temperature with the upper variance temperature set point. Then, if the sensed tissue temperature is equal to or greater than the upper variance set point, the system is converted to the COOLING mode as indicated in step 130, and the processor returns to decision step 118. If the tissue temperature is less than the upper variance set point, the processor continues to step 132 in the flowchart logic, and determines if the tissue temperature is equal to or less than the lower variance set point, whereby the system is converted to the HEATING mode and processor returns to decision step 118. Finally, if the tissue temperature is between the upper and lower variance set points, the system does nothing as indicated in step 134, and the processor returns to decision step 118.

Figure 4:
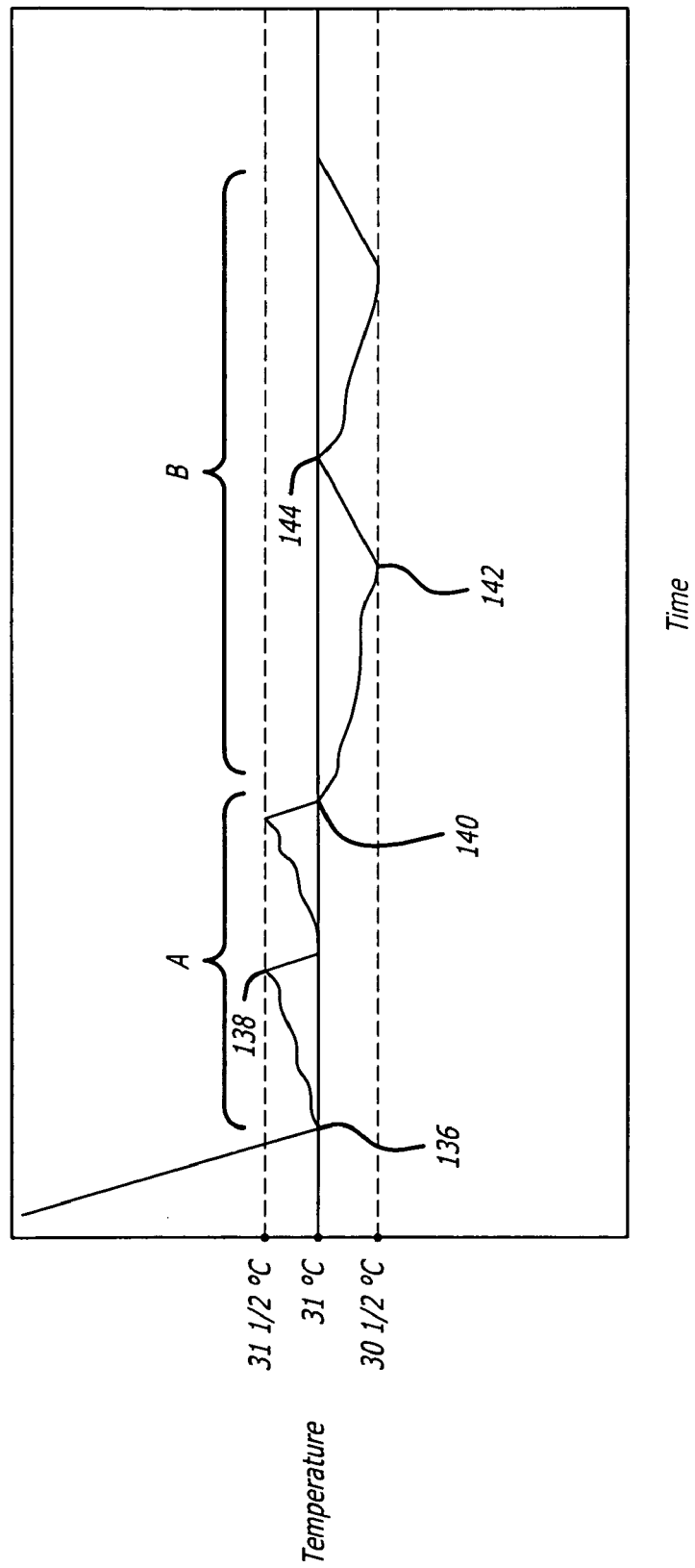
FIG. 4 is a graph of the sensed temperature of a target tissue or body fluid over time under the influence of the control scheme of FIGS. 3A-3B.

FIG. 4 is a graphical illustration plotting the fluctuating sensed tissue temperature over a period of time relative to the target temperature and variance set points. In the example, the target temperature is set at 31 degrees Celsius, with the upper and lower variance set points ½ degrees on either side. Initially, the sensed tissue temperature is greater than the target temperature, such as if the heat exchange catheter is placed in contact with blood at 37 degrees Celsius. The system is first placed in the COOLING mode so that the sensed tissue temperature is reduced until it equals the target temperature at 136, corresponding to steps 120a and 124 in FIG. 3A. In step 124, the heat exchanger is converted to the OFF mode, which results in the sensed tissue temperature climbing until it reaches the upper variance set point at 138, corresponding to step 130 in FIG. 3B, at which time the system begins cooling again. This cycle is repeated in the region indicated at A.

Eventually, the patient may be unable to maintain even the target temperature as shown by the temperature profile in the region indicated at B. For example, after the sensed tissue temperature reaches the target temperature at 140, and the heat exchanger is turned OFF, the sensed target temperature may continue to drift lower until it reaches the lower variance set point at 142. The controller logic senses this in step 132 of FIG. 3B, and converts the system to the HEATING mode. Subsequently, the sensed tissue temperature climbs to the target temperature at 144, and the system is again turned OFF, corresponding to steps 120b and 128 in FIG. 3B. Alternatively, depending on the patient and the situation, it may be that after the sensed tissue temperature reaches the target temperature and the heat exchanger is turned OFF, the patient's temperature may begin to increase until it rises to the upper variance set point temperature, at which point, as described in box 130 the heat exchanger begins to COOL. As can be appreciated, the sensed tissue temperature continues to fluctuate between the upper and lower variance set points in this manner.

The control scheme as applied to the system of the present invention has the advantage of allowing the operator to essentially input a desired temperature after which time the system will automatically regulate the tissue temperature until it reaches the target temperature, and will maintain the tissue temperature at that target temperature. The buffer range created by the upper and lower variance set points prevents the controller from turning the heater/cooler on and off or activating and de-activating the primary or secondary pumps in rapid succession, actions that would be potentially damaging to these electric devices. Moreover, the variance points, and other parameters used by the controller to regulate the cooling or heating power of the heater/cooler can be varied by the operator during the course of treatment to change the selected patient temperature or the ramp of the heating or cooling as needed to address specific therapeutic situations. A more sophisticated control scheme, such as the PID scheme described below, may also be employed.

Exemplary Control Unit

Figure 5A:
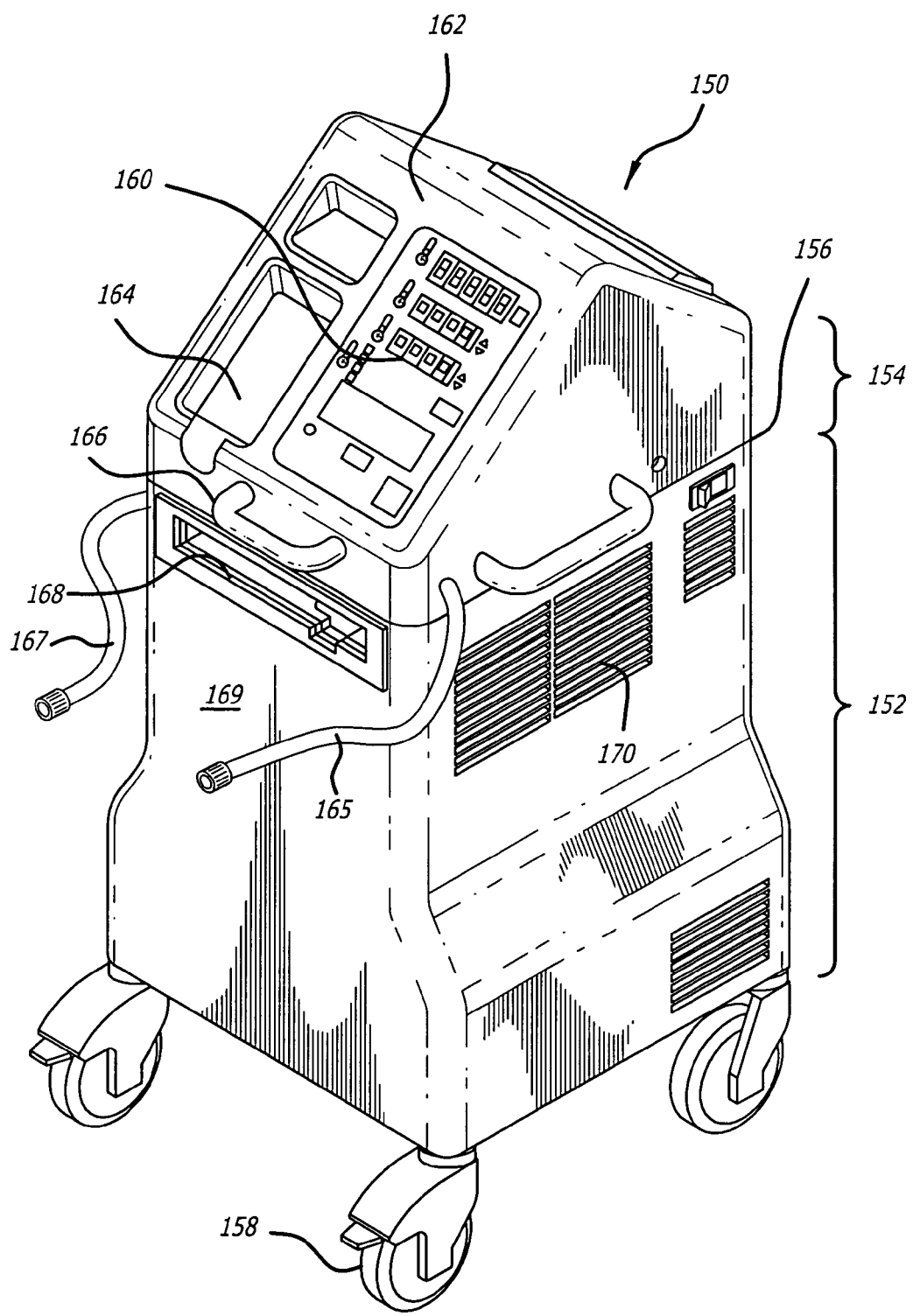
FIG. 5A is a perspective view of an exemplary re-usable control unit of the present invention.
Figure 5B:
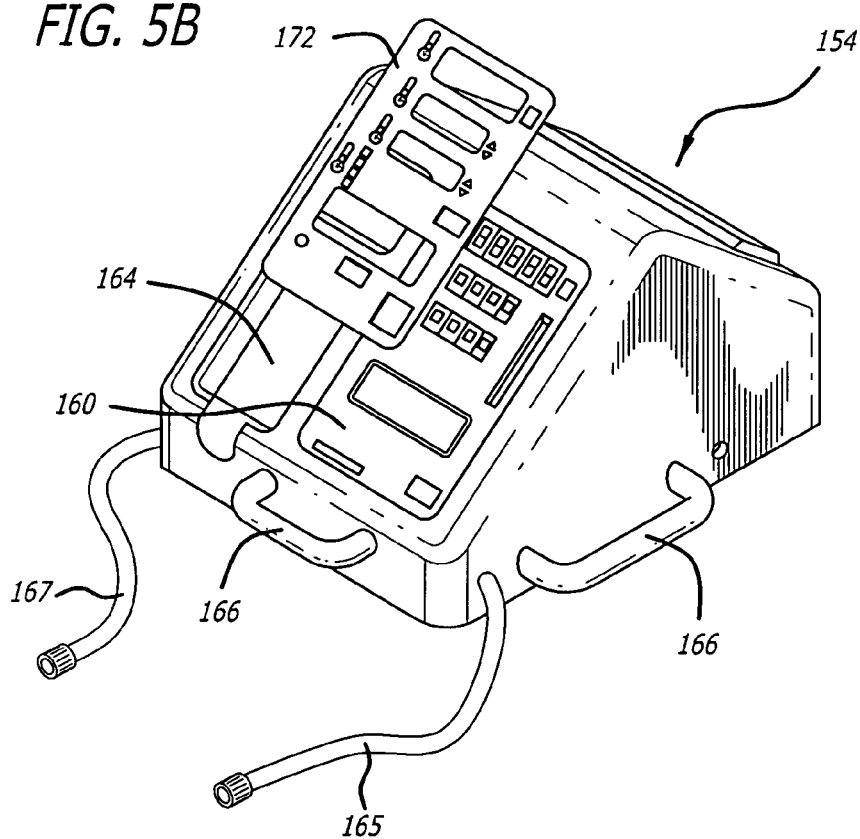
FIG. 5B is a perspective view of an upper portion of the control unit of FIG. 5A.
Figure 5C:
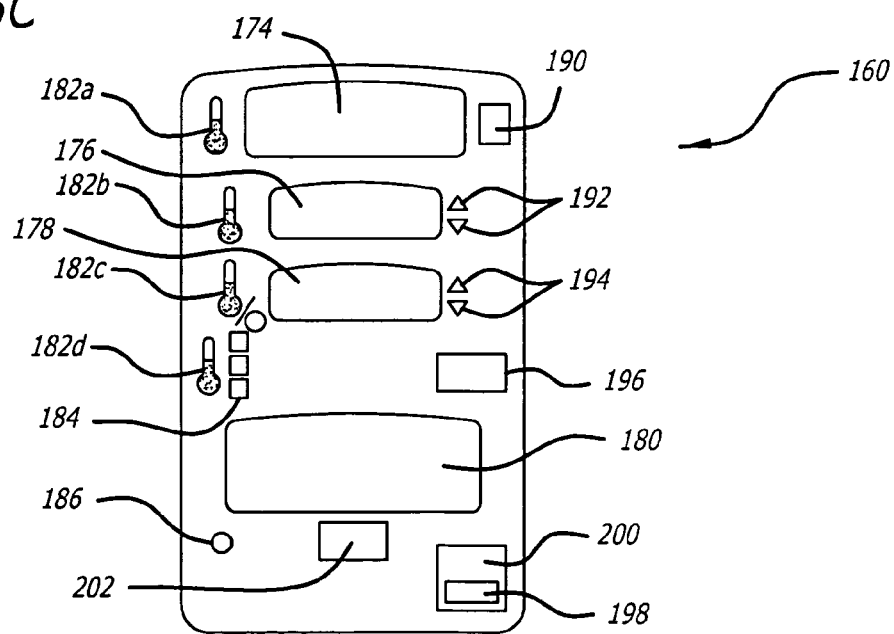
FIG. 5C is a plan view of an exemplary control panel for the control unit of FIG. 5A.

FIGS. 5A-5C are various views of an exemplary heat exchange control unit 150 of the present invention that is particularly suited for rapid temperature regulation of a patient.

As seen in the Figures, the control unit 150 comprises a vertically-oriented outer housing having a lower portion 152 and upper portion 154 separated at a generally horizontal dividing line 156 located close to the top of the unit. The control unit 150 is mounted on wheels 158 for ease of portability, with the wheels preferably being of the swivel type having foot-actuated locks. For ease of servicing, the upper and lower portions may be joined together with hinges 155 at the back so that the top portion may be lifted up and rotated back to expose the interior of the unit. In an exemplary embodiment, the control unit 150 has a height that enables an operator to easily access an upper control panel 160 without the need for significant bending. For example, the control unit 150 may have a total height of between approximately 2-3 feet, and preferably about 32 inches. The substantially horizontal cross-section of a majority of the control unit 150 may have widths of between one and two feet, although the lower portion 152 preferably widens at its lower end with the wheels 158 mounted on the lower corners to provide greater stability.

FIG. 5A illustrates the front and right sides of the unit 150 wherein the control panel 160 is visible on an angled upper panel 162 of the upper portion 154 front side. The angled upper panel 162 also defines a fluid container receiving cavity 164 adjacent the control panel 160. Further, a plurality of handles 166 may be provided to help maneuver the control unit 150.

A heat exchange cassette-receiving opening 168 is also provided on a front panel 169 of the control unit 150, just below the horizontal dividing line 156. As will be explained below, the opening 168 is sized and shaped to receive a cassette of the present invention, analogous to the heat exchange cassette-receiving opening 102 shown in FIG. 2. Likewise, the control unit 150 provides all of the features that were described above for the control unit 50 of FIG. 2, including equipment for heating or cooling the fluid in the cassette, a pump driver, a controller processor/microprocessor, and a manual input unit, namely the control panel 160.

Also shown in FIG. 5A are access points 165, 167. These access points are used to fluidly connect the heat exchanger to the primary fluid circuit. Access points may be configured as flexible tubing which is terminated by quick connect couplings that allow for rapid attachment and detachment of the access points from the cassette. The couplings may also be configured to seal upon disconnect, thus preventing loss of primary fluid from the primary fluid circuit. Additionally, the corresponding quick connect couplings disposed on the cassette may also be configured to prevent loss of primary fluid from the primary fluid side of heat exchanger in the cassette when the access points are detached. Alternatively, the quick connect couplings may be configured such that insertion of the cassette into the slot 168 causes quick connect fittings disposed on the cassette to automatically engage and fluidly couple with quick connect fittings within the housing to complete the fluid pathway of the primary fluid circuit so that primary fluid may be circulated through the primary fluid side of the heat exchanger in the cassette.

Because of the relatively high capacity for heating and cooling, the lower portion 152 of the control unit housing includes a plurality of vents 170 to facilitate convective heat exchange between the interior of the housing and the surrounding environment and to direct vented air away from the user or patient. The control unit housing may be manufactured of a number of suitably strong and corrosion-resistant materials, including stainless-steel, aluminum, or molded plastic. Desirably, the components of the control unit 150 are adapted to run on conventional power from a catheterization lab power outlet, for example.

The present invention also contemplates the use of two different control units in sequence, depending on need. For example, the control unit 150 of FIGS. 5A-5C having a relatively large heat transfer capacity and large housing can be used initially to rapidly alter the patient's body temperature. Subsequently, a smaller unit having an internal battery power source can be substituted for convenience and economy. Both the large and small control units desirably define the same sized and configured cavity for receiving a cassette of the present invention. In this manner, the cassette may be de-coupled from one unit, the patient transported with the cassette in place to another location without the first unit, and the cassette coupled to another unit for a subsequent operation/therapy. The present invention also encompasses a situation wherein the cassette is de-coupled from a first unit and then coupled to a second unit of the same size. This simply obviates the need to transport control units with the patient.

Exemplary Control Panel

FIGS. 5B and 5C illustrate in greater detail the upper portion 154 of the control unit 150, and in particular the control panel 160. FIG. 5B shows a facade 172 exploded from the control panel 160, with the facade shown in FIG. 5C having indicia printed thereon corresponding to various displays and buttons. (The reader will notice that the control panel 160 in FIG. 5C is an alternative embodiment from one shown in other drawings, and includes several added features and with several buttons and/or displays being slightly relocated). The following is a description of the physical characteristics of the control panel 160, with a description of an exemplary method of using the control panel to follow later in the description.

The exemplary control panel 160 of FIG. 5C provides a number of visual displays, including, from top to bottom along the centerline, a patient temperature display 174, a target temperature display 176, a cooling/warming rate display 178, and a system feedback/status display 180. Other desirable information may be displayed, either with an additional display, or alternating with information displayed on one of the screens shown here, or by user initiated request from one of the screens shown here. For example, by way of illustration but not limitation, if the ramp rate for heating or cooling the patient is set by the user, or is calculated by a control microprocessor, or the projected time to target temperature is calculated, those values may be shown. The larger displays for alphanumeric characters are preferably liquid crystal displays (LCD), while several light emitting diode (LED) status indicators are also provided. Several graphic icons are positioned adjacent the left of the upper three LCD displays 174,176, and 178, to indicate their respective display functions. Specifically, a patient temperature icon 182*a*, a target temperature LED 182*b*, and a cooling/warming rate LED 182*c* are provided. Just below the cooling/warming rate LED 182*c*, an operational mode LED 182*d* and associated vertical series of three mode indicators 184 are provided. Only one of the indicators 184 lights up at any one time, depending on whether the system is in the COOLING, WARMING, or MAINTAINING mode. In lieu of the mode indicators 184, the display 180 may carry the message COOLING PATIENT, WARMING PATIENT, or MAINTAINING so that the operator can easily identify the mode of functioning of the controller. There also may be only one patient temperature icon 182 which has a line of lights that streams upward if the unit is warming, downward if the unit is cooling, and blinks stationary if the unit is maintaining. Finally, a power on/off indicator LED is provided in the lower left corner of the control panel 160.

The control panel 160 also exhibits a number of input buttons including, in descending order on the right side of the control panel, a Celsius/Fahrenheit display toggle 190, a pair of target temperature adjustment buttons 192, a pair of cooling/warming rate adjustment buttons 194, a multi-function/enter button 196, and a mute audible alarm button 198. The mute audible alarm button 198 is nested within an LED alarm indicator 200. Finally, in the lower central portion of the control panel 160, a stop system operation button 202 permits instant shutdown of the system.

With reference again to FIGS. 5A and 5B, the housing includes a cassette receiver 168 which includes an internal cavity 242 into which a heat exchange cassette of the present invention can be inserted. In the preferred embodiment, a cassette is provided as described in greater detail below comprising a reservoir portion which is in fluid communication with a heat exchanger. Although not shown, a micro-switch is desirably provided in the slot 168 mounted on one of the walls of the cassette receiver cavity to indicate when the heat exchange cassette has been fully inserted into the internal cavity 242, and is engaged therein for proper operation of the system. Also not shown but well known in the relevant art, registration means such as pressure pins or balls and mating detents may be provided in the control unit and cassette respectively to aid in the correct relative positioning between the cassette and the control unit. This arrangement also provides, in some embodiments, for simultaneous engagement of the motor and fluid connections to the cassette, providing for easy insertion and setup of the cassette.

Figure 6:
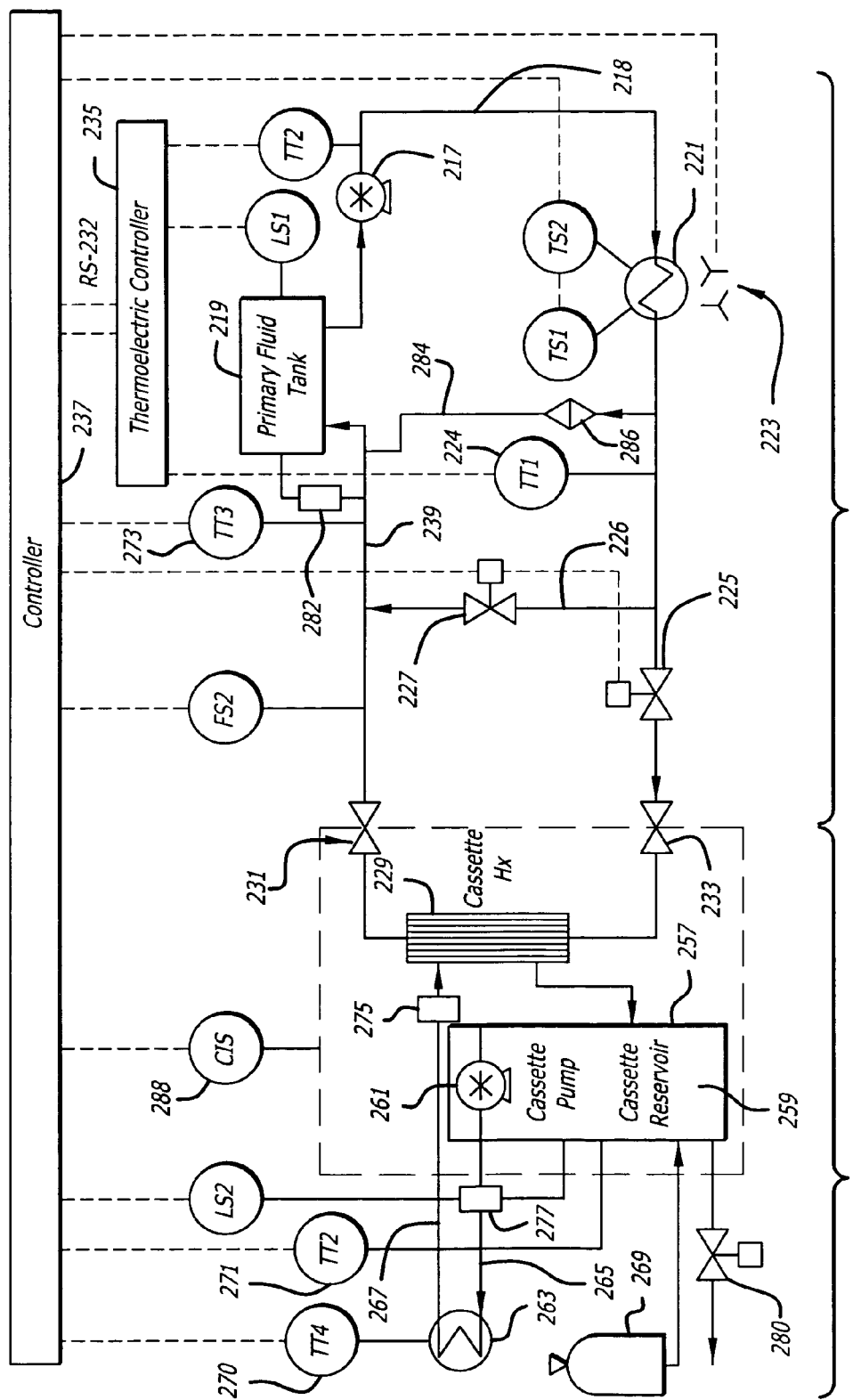
FIG. 6 is a schematic view of an embodiment of the system of the present invention showing a heat exchanger in fluid communication with a positive pressure side of a primary fluid circuit pump.

Referring now to FIG. 6, the primary and secondary cooling circuits utilized by a preferred embodiment of the present invention will now be described. In the embodiment shown, a primary fluid circuit 215 comprises a pump 217 that draws primary circuit fluid from a primary circuit reservoir 219. The primary circuit fluid is pumped under pressure through line 218 through a primary circuit heat exchanger 221. As described above, primary circuit heat exchanger may include a heater/cooler, such as thermoelectric heater/cooler for heating or cooling the primary circuit fluid. A blower 223 may be included to assist in removal of excess heat generated by the heater/cooler or to provide the thermal gradients required for proper operation of the heater/cooler. Alternatively, other means for heating or cooling the primary circuit fluid may be used, such as a water bath that can be heated or cooled as desired, or by using a suitable compressor operating a refrigeration cycle that is familiar to those skilled in the art. For example, use of refrigeration to cool the primary fluid would require some way to warm the primary fluid, such as, for example, a heat pump, resistive heating, radio frequency (RF), microwave or other suitable heating method. Similarly, cooling of the primary circuit can be provided by an ice bath, or other suitable stored energy source such as compressed or liquefied gas, or endothermic reactive chemicals. The primary fluid circuit may be any suitable fluid or gas, and is not required to be bio-compatible. In other instances, the primary fluid circuit may be bio-compatible, such as for example, saline. The fluid may also be a suitable slurry, such as slush of brine or other fluid.

The temperature of the fluid circulating within the primary fluid circuit line downstream of the heat exchanger 221 is sensed using a suitable temperature sensor, such as, for example, a thermocouple or thermistor 224, 273, that provide temperature signals to, for example, a thermoelectric controller 235. Alternatively, the temperature signals may be sent to system controller 237. Those skilled in the art will understand that the function of thermoelectric controller 235 may be included in the functions carried out by system controller 237, and thus the scope of the invention does not require a separate thermoelectric controller.

In this embodiment, temperature sensor 273 monitors the temperature of the primary fluid returning to the reservoir 219. The signals from this sensor may be used to continuously monitor and calculate the cooling or heating power being delivered. The power may be calculated because the inlet temperature to the heat exchanger 229 is measured by temperature sensor 224, and the pump speed, and thus the speed of flow through the heat exchanger, is also known. The calculation of power from these values is well known by those skilled in the art. Monitoring the power is useful because a change in power may indicate a problem, either in the primary loop or the secondary cooling loop. For example, should the primary fluid circuit experience a drop in fluid flow or a decrease in heat exchange, the temperature of the primary circuit sensed at temperature sensor 224 would decrease when cooling, or rise when heating. Upon receiving the temperature signal from sensor 224, the controller may cause a variety of actions to occur to ensure the safety of the patient. For example, the controller may stop the pump and cause an alarm to be sounded.

In the depicted embodiment, the primary fluid circuit 215 includes a valve 225 and a valve 227 to control the path the fluid circulating within the primary fluid takes. In this embodiment, valve 225 is a solenoid valve that is normally closed, and valve 227 is a solenoid valve that is normally open. Both valves 225 and 227 are controlled by signals from controller 237. In this arrangement, fluid exiting the primary heat exchanger 221 is diverted by valve 225 into cut off line 226, where normally open valve 227 provides an open pathway for the circulating fluid to return to primary fluid reservoir 219 through line 239. In this manner, the present invention provides a closed loop that allows for continuous pumping of primary circuit fluid through primary heat exchanger 221 and into primary fluid circuit reservoir 219 when heat exchanger 229 is not connected to the system, allowing the temperature of the primary fluid circuit 215 to be heated or cooled as desired, and then maintained at a temperature, ready to provide a large stored amount of heating or cooling when the operator controls the system to beginning heating or cooling the blood of the patient. The advantages of such a system will be discussed in more detail below.

The interface between primary fluid circuit 215 and secondary fluid circuit 255 is provided by heat exchanger 229. As shown, heat exchanger 229 provides the means to transfer heat energy, either in heating or cooling mode, between the primary and secondary fluid circuits 215 and 255.

Heat exchanger 229 includes a pair of fluid pathways, which be thought of as intermediate fluid pathways. These two intermediate pathways, a primary intermediate pathway and a secondary intermediate fluid pathway, are physically separated from each other, but are in thermal communication with each other. This provides for the exchange of heat energy between the intermediate fluid pathways, while preventing the possibility of contaminating the secondary heat exchange fluid which may flow into a patient with primary fluid circuit fluid, which may or may not be biocompatible. Similarly, the physical separation of the primary and secondary intermediate fluid pathways prevent the contamination of the primary fluid circuit should blood or other bodily fluids invade the secondary fluid circuit.

These intermediate fluid pathways, when connected to their respective primary or secondary fluid circuits, increase the volume of these circuits. This provides several advantages that will be discussed in more detail below.

Secondary fluid circuit 255 comprises a cassette 257 that includes heat exchanger 229, a secondary fluid circuit reservoir 259 and secondary fluid circuit pump 261. Fluid contained within secondary fluid circuit 255 is drawn from reservoir 259 by pump 261 and forced down supply line 265 to a heat exchanger 263, such as a balloon mounted on a distal end of a catheter, as described previously, that has been positioned within a patient's blood vessels. After the secondary fluid has passed through heat exchanger 263, the fluid flows through return line 267 to heat exchanger 229 and then back into reservoir 259 to complete the closed loop of the secondary fluid circuit 255. In an alternative embodiment, the order of heat exchanger 263 and heat exchanger 229 are reversed so pump 261 forces fluid through the secondary side of heat exchanger 229 and then down supply line 265, and return line 267 empties into reservoir 259. A separate fluid supply 269, such as a bag of saline, may also be in fluid communication with the secondary fluid circuit through appropriate lines and valves to provide a source for additional secondary fluid should for priming the secondary fluid circuit or to make up any secondary fluid that is inadvertently lost during treatment of a patient. Fluid supply 269 and reservoir 259 provide compliance for the secondary fluid circuit to accommodate volume changes in the fluid circuit due to heating and cooling of the fluid circuit. Similarly, the primary fluid tank 219 provides compliance for the primary fluid circuit.

The temperature of the secondary fluid circulating through the secondary fluid circuit may be measured using temperature sensors, such as sensors 270, 271, whose signals are communicated to controller 237. These, and other signals, may then be used by controller 237 to control the heating and cooling of the patient by controlling the heating and cooling of the primary fluid circuit or to provide an alarm or take other action should the values of the signals sensed by sensors 270, 271 indicate that the device is not functioning properly. Additionally, controller 237 may control the speed of pump 261 independently, or in conjunction with controlling heat exchanger 221, to heat or cool the patient to a desired temperature at a desired rate of temperature change.

The primary fluid circuit side of heat exchanger 229 is removably connected to the primary fluid circuit using quick connect/shutoff valves 231, 233. Use of these quick connects allows the heat exchanger 229 to be removed from the primary fluid circuit without a substantial loss of primary fluid circuit fluid. Additionally, primary circuit fluid will not flow into heat exchanger 229 unless controller 237 provides a valve open signal to normally closed valve 225. As will be apparent to those skilled in the art, when the controller 237 provides a valve open signal to normally closed valve 225, controller 237 also provides a valve closed signal to normally open valve 227 located in cutoff line 226 to close off cutoff line 226 from the primary fluid circuit, ensuring that all primary fluid circuit is directed through heat exchanger 229.

As noted above, this arrangement is advantageous as it provides for continuous circulation of primary fluid within primary fluid circuit 215, which allows the temperature of the primary fluid circuit 215 to be heated or cooled to a desired temperature, and then held at that temperature, even if a patient is not being treated at the time. This is particularly advantageous where a patient requires rapid heating or cooling. In some prior art systems, the cooling media used to cool the patient by necessity was a room temperature at the beginning of treatment. Thus, the rate of cooling or heating of the patient was dependent on the ability of the system to add heat to or remove heat from the cooling media. This could be problematic in the event rapid cooling of the patient was desirable, since in many cases the system was not capable of removing heat from the patient's blood at a rate sufficient to achieve the desired cooling rate.

The system of the present invention addresses this need by providing a reservoir of already cooled (or heated, depending on the needs of the emergency) primary circuit fluid. Since the primary fluid is already cooled, the rate of cooling no longer depends solely on the cooling capacity of heater/cooler 221, but rather on the combined cooling capacity of the pre-cooled fluid and heater/cooler 221. In effect, this embodiment of the present invention provides what the inventor has identified as a "turbo boost" in the heating/cooling capacity of the system that is helpful where a patient needs to be rapidly cooled or warmed to provide an enhanced therapeutic effect. The relative amount of "turbo boost" can be adjusted by adjusting the temperature of the primary fluid in the primary fluid reservoir, or by increasing the size of primary fluid reservoir 219, or both.

In an alternative embodiment, the supply line 265 and the return line 267 may include couplers, such as luer lock fittings 275, 277. Such an arrangement is advantageous in that it allows the cassette to be disconnected from the catheter 263 during treatment of the patient, if necessary. In another embodiment, the heat exchanger may include connections for connecting a sensor line from sensors associated with the catheter such that the sensor line is connected to the command processor at or about the same time that the access points are connected, thus facilitating rapid set up of the system.

In yet another alternative embodiment, the access points in the primary fluid circuit allow the primary fluid reservoir to be easily filled with primary fluid. Additionally, the access points allow for draining the primary fluid reservoir of primary fluid to facilitate replacement of the reservoir, shipment of the device as otherwise deemed necessary for convenience or safety.

In still another embodiment, the primary fluid circuit may include a means for ensuring that the electrical resistivity of the primary fluid remains above a predetermined threshold to ensure the electrical isolation of the primary fluid circuit and the safety of the patient. One means for accomplishing this is to include a de-ionizing cartridge 282 containing a suitable ion-exchange resin in the primary fluid circuit. The flow through the de-ionizing cartridge may be controlled to allow the entirety of the fluid circulating in the primary fluid circuit to flow through cartridge 282, or it may be controlled to treat only a portion of the fluid returning through the primary loop into the tank 219.

In yet another embodiment, the access points allow the heat exchanger to be easily and rapidly disconnected from the primary fluid circuit in the event of a power failure or other problem. In this manner, an alternative method of providing primary fluid can be used, such as, for example, circulating ice water through the primary fluid side of the heat exchange using a system suitable configured to do so.

To protect the primary fluid circuit 215 and pump 217 against overloads where valves 225 and 227 are both closed, an internal bypass loop 284 may be disposed in the primary fluid circuit. Bypass loop 284 may include a check valve 286 which is set to open a predetermined pressure that is low enough to prevent damage to the pump. The inclusion of the bypass loop is also advantageous in that any blockage of the heat exchanger 229 or inadvertent disconnection of quick couplings 231 or 233, that results in increased primary circuit pressures which may damage the heat exchanger 229 may also be relieved by setting the opening pressure of check valve 286 at an appropriate level.

An active or passive vent valve 280 may also be included in the secondary fluid circuit. Inclusion of this valve is useful in venting air from the secondary fluid circuit to assist in priming the secondary circuit with secondary circuit fluid prior to use of the cassette.

In an alternative embodiment, monitoring and controlling the performance of the system may be carried out by monitoring the temperature in the primary fluid circuit only. Monitoring the temperature of the primary circuit provides information to the controller that may be used to calculate the amount of heat energy that needs to be added to or subtracted from the primary fluid circuit so as to drive the heat exchange ability of the secondary fluid circuit to alter the temperature of the patient's tissue or blood.

Figure 7:
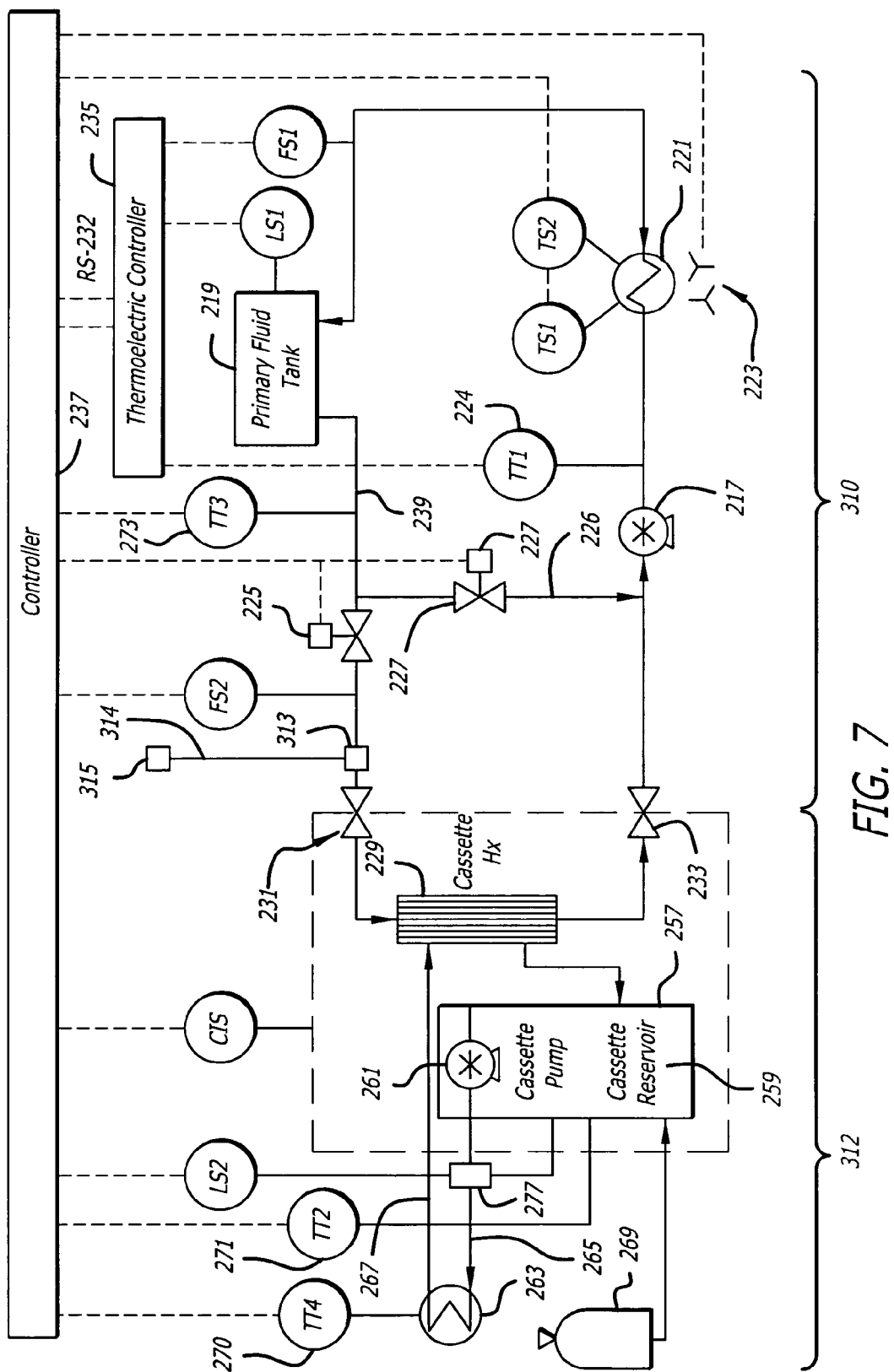
FIG. 7 is a schematic view of another embodiment of the system of the present invention showing the heat exchanger in fluid communication with a negative pressure side of the primary fluid circuit pump.

FIG. 7 depicts an alternative embodiment of the system of the present invention. In this embodiment, the flow through primary fluid circuit 310 and secondary fluid circuit 312 are altered. As depicted, primary fluid circuit pump 217 now draws fluid through heat exchanger 229 rather than pumping fluid through it as shown in FIG. 6. Moreover, normally closed valve 225 is located between reservoir 219 and heat exchanger 229. Thus, heat exchanger 229 is located on the negative pressure side of pump 217. Similarly, secondary fluid flow through heat exchanger 229 is reversed, necessitated by the change in flow direction of the primary fluid circuit. An active or passive vent valve 313, vent line 314 and vent filter 315 are also in fluid communication with the primary fluid circuit on the negative pressure side of pump 217.

There are several advantages of this arrangement. One inconvenience posed by using a removable heat exchanger 229 is the need to empty the heat exchanger 229 of primary circuit fluid when the heat exchanger 229 is detached from the primary fluid circuit. This arrangement addresses that inconvenience by allowing pump 217 to empty heat exchanger 229 of primary circuit fluid before the heat exchanger is detached. For example, when the heat exchanger is to be detached after providing treatment to a patient, an operator, using the manual input unit (FIG. 5), can direct the controller 237 to send a valve close signal to valves 225 and 227 and a valve open signal to vent valve 313. This effectively closes off the supply of primary fluid from the reservoir feeding pump 217, but opens a path to the air through vent valve 313, vent line 314 and vent filter 315. This allows the pump to suck the primary fluid from heat exchanger 229 and pump the fluid into reservoir 219 for storage. When the primary side of heat exchanger 229 has been exhausted of primary fluid, the controller 237, either automatically having sensed that the fluid is exhausted, or after receiving a manual command from the operator, sends a valve close signal to vent valve 313 and a valve open signal to valve 227 to close off the vent line and restore fluid flow through cutoff line 226. It will be understood that while the above has been described with reference to various valve open and valve close signals, where normally open or normally closed valves are used, no signal will be necessary to place the valves in their normal state. Rather, the controller may simply stop providing a signal that places the valve in an other than normal state. In an alternative embodiment, the vent valve could be in communication with the inlet side of the pump 217 in FIG. 6. Such an arrangement would require an additional valve. However, this arrangement, while workable, is not preferable.

A further advantage to the embodiment of the present invention depicted in FIG. 7 is that placing heat exchanger 229 on the negative pressure side of the pump facilitates keeping the secondary primary circuit at an increased pressure relative to the pressure of the primary fluid circuit, which enhances the safety of the system should a leak develop in the primary fluid circuit of heat exchanger 229 by preventing encroachment of the primary fluid into the secondary fluid circuit. Alternatively, the secondary circuit could be controlled so as to have a higher pressure than the primary circuit by having the pump push secondary fluid through the heat exchanger 229 and then through the catheter.

Exemplary Electronic Control Circuit

As an alternative to the control system described in conjunction with FIGS. 3A-3B and the graph of FIG. 4, the controller may employ a cascading PID control scheme. In such a scheme, a control system is provided that may be divided into two sections: (a) a Bulk PID control section which takes input from the user (in the embodiment shown, RAMP RATE and TARGET TEMPERATURE) and input from the sensors on the patient representing patient temperature, and calculates an intermediate set point temperature (SPI) and an output signal to the primary fluid PID control; and (b) the primary fluid PID control, that receives input from the bulk PID control section and from a sensor representing the temperature of the primary fluid, and generates a signal that controls the temperature of the TE cooler by varying the power input to the TE cooler. The primary fluid circulates in heat transfer proximity to the TE cooler, so the primary fluid PID essentially controls the temperature of the primary fluid. In this way, the control scheme is able to automatically achieve a specified target temperature at a specified RAMP RATE based on input from sensors placed on the patient and the logic built into the controller. Additionally, this scheme allows the unit to automatically alter the patient temperature very gradually the last few tenths of a degree to achieve the target temperature very gently and avoid overshoot or dramatic and potentially damaging swings in the electronic power to the TE cooler. Once the target temperature is achieved, the system continues to operate automatically to add or remove heat at precisely the rate necessary to maintain the patient at the target temperature.

Figure 8:
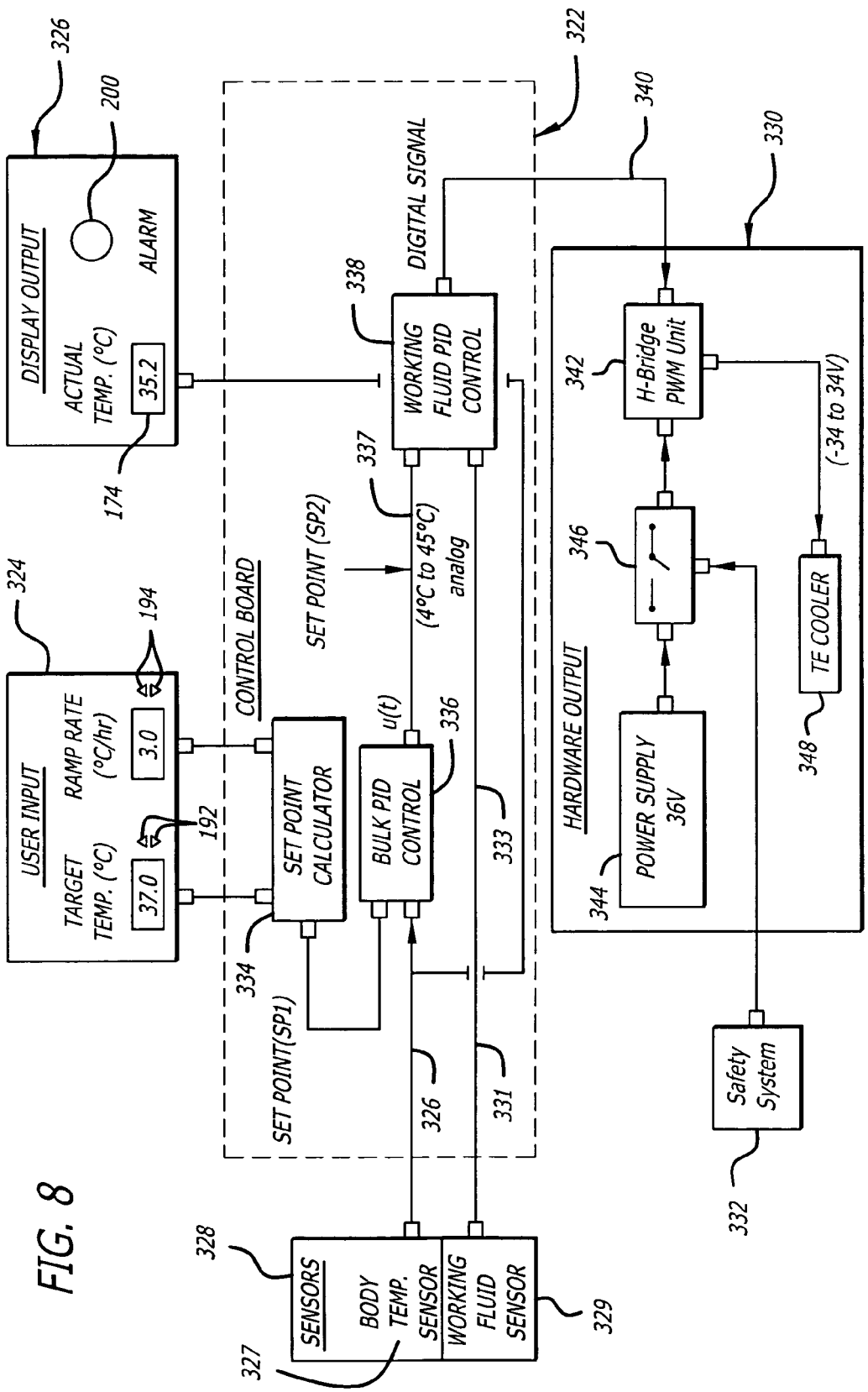
FIG. 8 is a schematic diagram of exemplary components of the present invention, illustrating communication and feedback interconnections therebetween.

Specifically, this is achieved as illustrated in FIG. 8. FIG. 8 illustrates an exemplary control schematic of components of the present invention specifically adapted for use in control unit 150 of FIG. 5A, but applicable to any control unit described herein. Some of these elements correspond to elements identified previously, and thus, where appropriate, reference numbers will be repeated for clarity. In general, the control circuit includes a control board having a number of logical components indicated within the dashed line 322, a user input 324, a display output 326, a plurality of sensors 328, a number of elements of electronic hardware indicated within the box 330, and a safety system 332. The user inputs 324 and display outputs 326 were described above with respect to the control panel 160 of FIG. 5C. The two user inputs 324 applicable to the control circuit in this embodiment are the target temperature adjustment buttons 192 and cooling/warming rate adjustment buttons 194. The display outputs 326 applicable to the control circuit are the patient temperature display 174 and the alarm display 200, but may include a number of other displays for various feedback to the user. A plurality of sensors 328 may be provided, including at least a sensor 327 that senses the patient's actual body temperature and generates a signal represented by line 326, and a sensor 329 that directly or indirectly senses the temperature of the primary fluid and generates a representative signal 331.

After the system is primed, a set point temperature (SPI) is determined with a set point calculator 334 using the target temperature and the desire ramp rate as inputs. This set point temperature represents an interim target temperature that the system will achieve at any given time, for example 0.1° C. each 6 minutes, if the ramp rate is 1° C. per hour, starting with the initial patient temperature. This set point temperature is transmitted to a Bulk PID control section 336 of the control board. The Bulk PID control 336 also receives input from the body temperature sensor 327.

Based on the differential between the SP1 and actual body temperature, if any, the Bulk PID control 336 raises or lowers the temperature specified for the heat exchange fluid that will be circulated through the secondary fluid circuit so as to induce a change to the patient temperature at the specified ramp rate. That is, a value for the desired primary fluid temperature, or a second set point temperature (SP2), is transmitted to a primary fluid PID control unit 338 as illustrated at 337. The primary fluid PID control unit 338 also receives input from the temperature sensor 329 for the primary fluid as illustrated at 333. The primary fluid PID control unit 338 compares the sensed primary fluid temperature with the desired primary fluid temperature transmitted from the bulk PID control to determine a differential, if any. Based on this differential, the primary fluid PID control 338 transmits a digital signal as illustrated at 340 to an "H-Bridge" polarity switching unit 342, which directs power of an appropriate magnitude and polarity to the TE cooler 348 to cause the TE heater/cooler to be heated or cooled to drive the temperature of the primary fluid to an appropriate level to drive the temperature of the secondary fluid to heat or cool the temperature of a patient's tissue or blood toward the desired temperature, or maintain it at that temperature.

The polarity switching unit 342 receives power from a source 344 and transforms that power to the appropriate magnitude and polarity requested by the primary fluid PID control unit. Between the power source and the polarity switching unit is a safety relay 346 actuated by the safety system 332 that will, in the absence of a safety issue, transmit the power from the power source 344 to the polarity switching unit 342. If the safety system 332 is aware of a safety issue, for example if a low fluid level is sensed, it may direct the safety relay 346 to open and prevent power from the power supply 344 from being directed to the TE cooler 348. In the absence of any safety issue, however, the polarity switching unit 342 transmits the power to the heater/cooler unit 348 in accordance to the request from the primary fluid PID control unit. Various subsystems of the present invention provide input to the safety system 332, and will be described below when introduced.

The control circuit includes logic that permits rapid heat exchange when the target temperature and the sensed body temperature are relatively far apart, and which slows down the rate of heat exchange as the sensed body temperature nears the target temperature. As the sensed patient temperature and the SP1 become very close, the Bulk PID will dictate only a very small change in the primary fluid temperature, and thus the rate of change will become smaller and smaller as the SP1 becomes very close to the sensed patient temperature until the rate of change is essentially non-existent. In this way, the patient temperature may be very gently is heated or cooled the last few tenths of a degree, avoiding overshoot or dramatic swings from heating to cooling when the body temperature is at the target temperature. As the input TARGET TEMPERATURE is reached, the SP1 and the TARGET TEMPERATURE are essentially the same, and the system operates to set the power to the TE cooler at a level that maintains the necessary primary fluid circuit temperature to hold the patient temperature at the TARGET TEMPERATURE. In this way, the system will work to maintain a target temperature with the primary fluid maintained at just the right temperature to add or remove heat at the precise rate necessary to maintain that target temperature as essentially a steady state.

The primary fluid PID control 338 samples its respective inputs at a rate of 10 times a second and updates the output to the polarity switching unit 342 at a rate of once every second, and thus the trends of changing patient temperature are constantly monitored and adjusted. The Bulk PID control 336 samples its inputs at the same rate, and thus a new target temperature or a new ramp rate can be specified by the user with nearly instantaneous system response.

The controller of the present invention may also be used to control other aspects of the cooling system. For example, in one embodiment, when the temperature of the patient approaches within 0.3 degrees of the target temperature, the controller may decrease the output of the secondary fluid circuit pump, may decrease the output of the primary fluid circuit pump, and/or reduce the speed of the fan/blower on the primary circuit to reduce the amount of noise generated by the apparatus.

Exemplary Heat Exchange Unit

Figure 9:
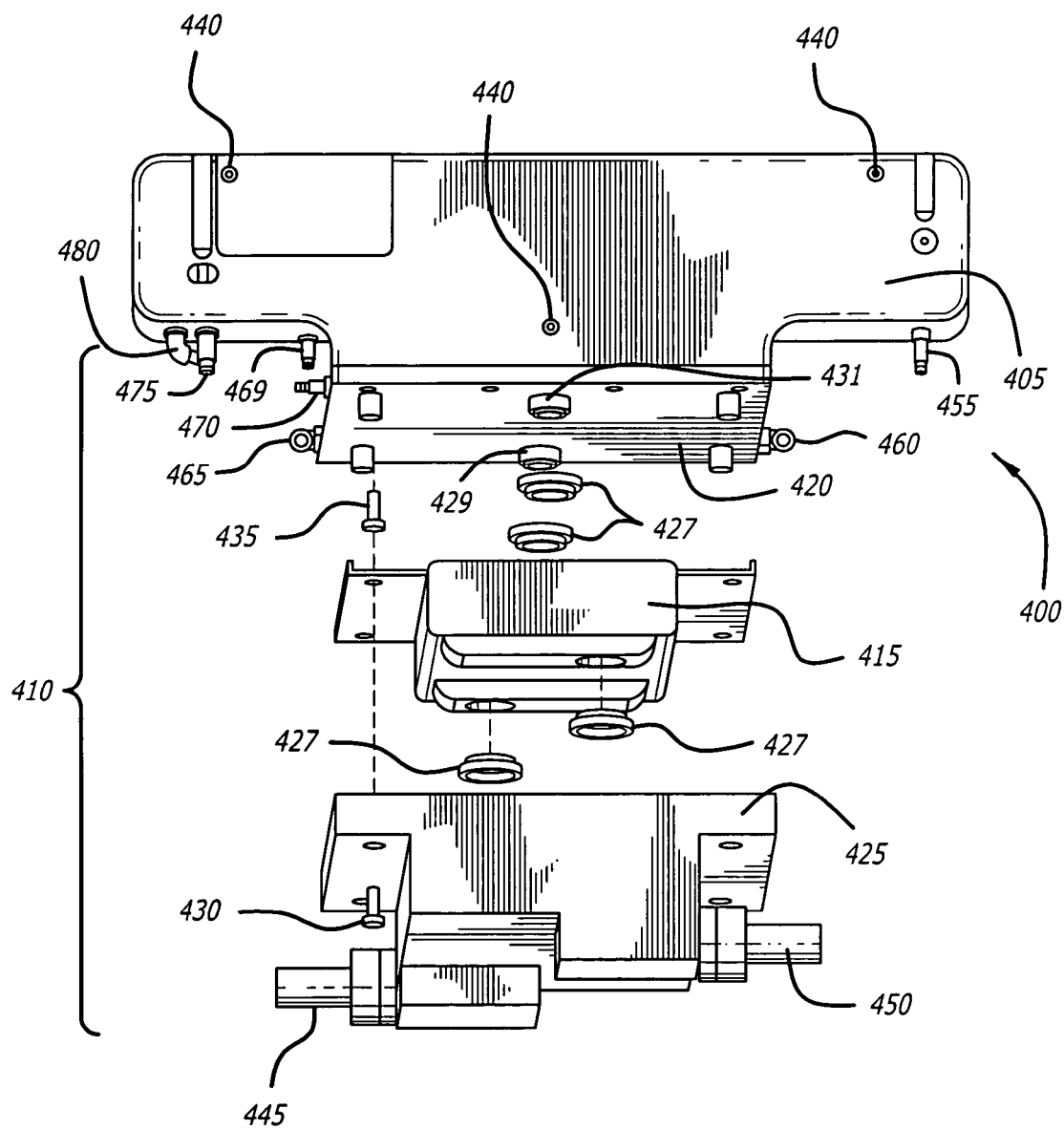
FIG. 9 is an exploded view of an embodiment of the heat exchange cassette of the present invention.

FIG. 9 is an exploded view of an exemplary embodiment of a heat exchange cassette 400 of the present invention. Heat exchange cassette 400 includes a cassette section 405 containing a reservoir compartment, secondary circuit pump and a heat exchanger 410 for exchanging heat energy between the primary and secondary fluid circuits.

Heat exchanger 410 comprises a heat exchange section 415 disposed within a cavity formed between a base plate 420 and cover 425. O-ring bushings 427 are used to seal fluid passageways inside of the cavity to facilitate fluid flow though the heat exchange section 415. The cover 425 is held to the base plate 420 by connector 430, which may be a threaded screw or bolt, or other device capable of attaching the base plate to the cover. The entire heat exchanger 410 is attached to the cassette section 405 using suitable connectors 435. FIG. 9 also shows connectors 440 which releasably attach a mounting cover to the reservoir compartment.

The base plate 420 also includes two fluid channels (not shown), to be discussed in more detail below. The inlet of the first fluid channel receives secondary fluid returning from the catheter and the inlet of the second fluid channel receives priming fluid to fill the heat exchanger with secondary fluid before use. The outlets of both the first and second fluid channels are fluidly connected to the inlet 429 of the heat exchanger. Heat exchanger outlet 431 is fluidly connected to the reservoir in the cassette section 405.

Also shown in FIG. 9 are a variety of fluid connectors for completing the fluid paths of the primary and secondary fluid circuits. For example, connectors 445 and 450 are mounted on cover 425 and are used as input and output ports for communicating fluid through the primary circuit side of the heat exchanger 415. Similarly, barb 455 is disposed in the output fluid path of the secondary fluid circuit pump, and provides for connection to the supply line that provides secondary fluid to the balloon of the catheter that is used to heat or cool a patient's blood. Barb 460 receives the return line from the catheter and provides an input though the first fluid channel in the base plate 420 into inlet of the secondary side of heat exchanger 415.

After secondary circuit fluid has flowed through heat exchanger 415, the secondary fluid exits the heat exchanger 415 through outlet 431 and flows out barb 470 into the reservoir of cassette section 405 through barb 480. Barbs 465 and 469 provide access to the secondary fluid circuit to prime the secondary fluid circuit with secondary fluid, and barb 475 allows the reservoir in cassette section 405 to be vented.

Figure 10:
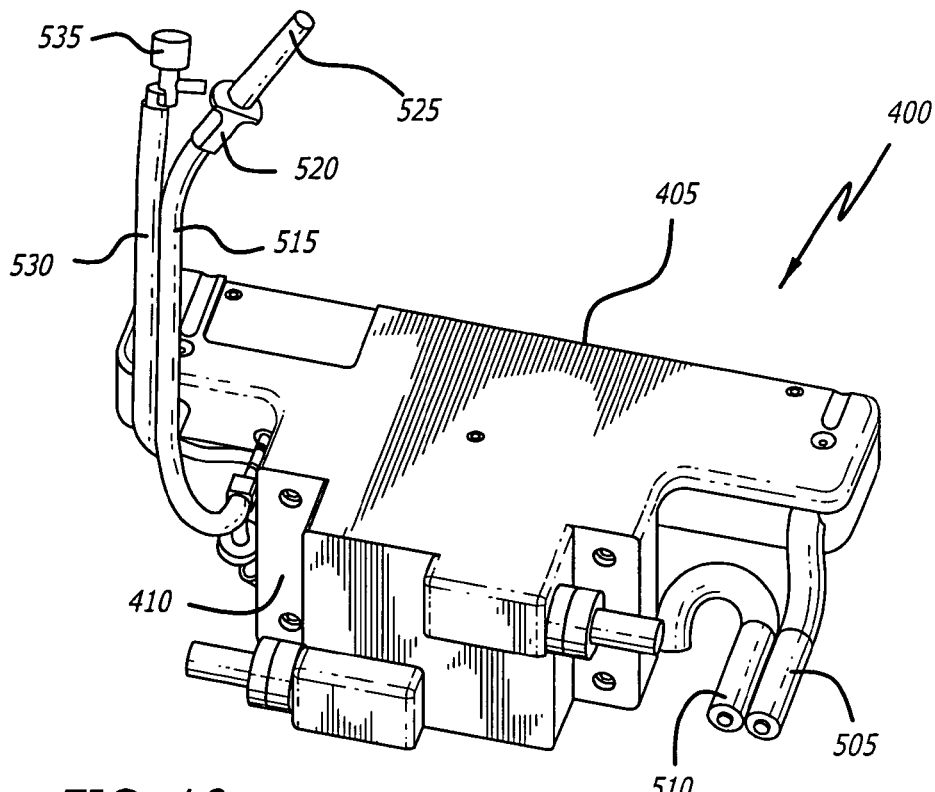
FIG. 10 is a perspective view of the embodiment of FIG. 9.
Figure 10A:
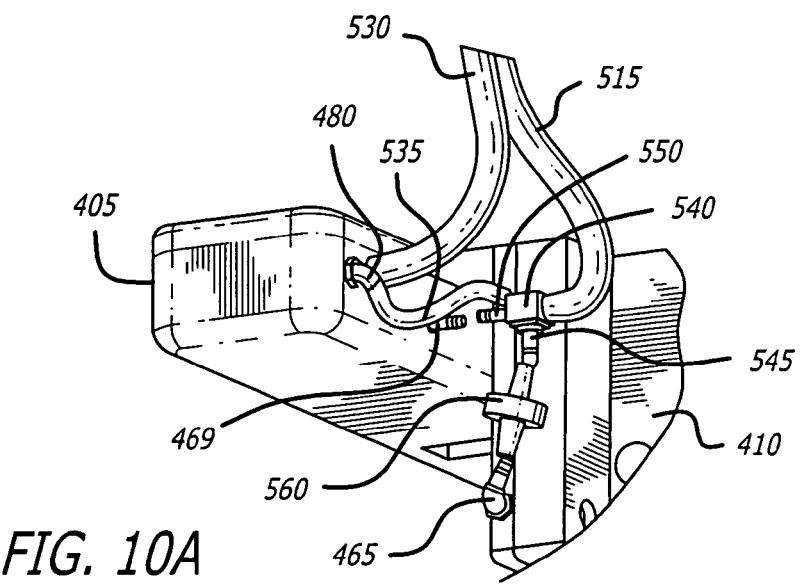
FIG. 10A is an enlarged perspective view of a portion of the embodiment of FIG. 10.

FIGS. 10 and 10A depict an exemplary embodiment showing the secondary circuit tubing connections to the heat exchange cassette 400. Supply tubing 505 to the balloon catheter is connected to barb 455 (FIG. 9), and return tubing 510 is connected to barb 460. As described above, barb 460 is connected via the first fluid channel in base plate 420 to the inlet 429 of the secondary side of the heat exchanger. Fluid supply line 515, which includes a spike 520 covered by spike cover 525, is connected to splitter block 540. Splitter block 540 includes barb 550 which is connected by a short length of tubing (not shown) to barb 469. A low pressure check valve 560 is disposed between and connects barbs 545 and 465. Barb 465 is fluidly connected to the second fluid channel in base plate 420, and provides fluid access to the secondary side of the heat exchanger to allow the heat exchanger to be primed with secondary circuit fluid when necessary. Vent line 530, which includes an active or passive vent valve 535 is connected to barb 475.

The secondary fluid circuit may be primed with secondary fluid by inserting spike 520 into a fluid source. Fluid flows into spike 520 and through line 515 and into splitter 540, where the fluid stream is divided. Fluid then flows into the heat exchanger through check valve 560 and barb 465 and into the second fluid channel in base place 520 and finally into the inlet 429 of the heat exchanger. Simultaneously, fluid flows into the reservoir of the cassette section through barb 469. Check valve 560 is a one way valve that allows fluid to flow during priming, but prevents flow in the opposite direction, as would occur during operation of the secondary fluid circuit when fluid under pressure from the return line would be present at the inlet of the heat exchanger. This arrangement is advantageous in that it allows the reservoir and heat exchanger to be primed simultaneously.

In another embodiment, lines 515 and 530 may include valves that may be automatically actuated to facilitate automatic priming of the secondary fluid circuit. In one preferred embodiment, lines 515 and 530 run through a electrically actuatable clamp. When the operator of the system presses a button, for example, a PRIME button on the controller or controller display, the controller commands the clamp to open. At this time, fluid flows from the fluid source into the reservoir, and air is allowed to vent from the system. Typically, the fluid from the fluid source fills the reservoir via gravity, but a pressure cuff, or other similar means, may be applied to the fluid source to increase the rate of fluid flow, and thus decrease the time needed to prime the secondary fluid circuit. When the level in the reservoir is determined to be full, utilizing the sensing system previously described, controller closes the clamp or valve controlling flow through vent line 515. The clamp or valve on line 530 may remain open to allow the fluid source to accommodate volume changes that occur due to temperature changes and or pressure changes in the secondary fluid circuit during operation.

Figure 11A:
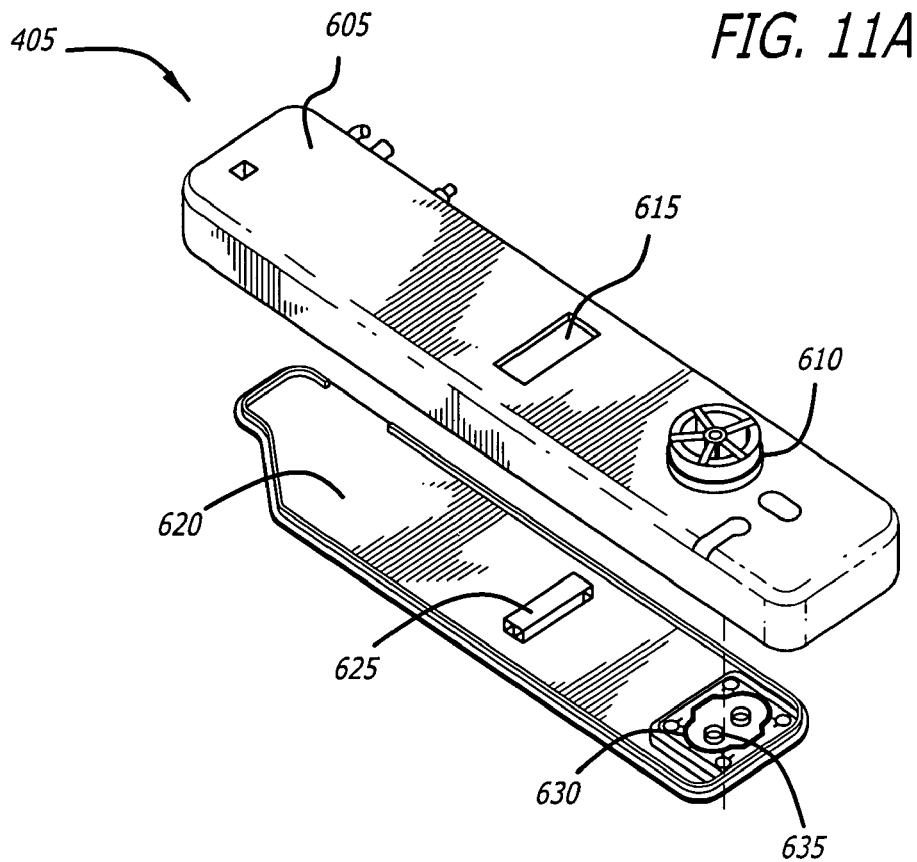
FIG. 11A is an exploded perspective view of a cassette portion of the embodiment of FIG. 9 showing an exterior view of the cassette portion.
Figure 11B:
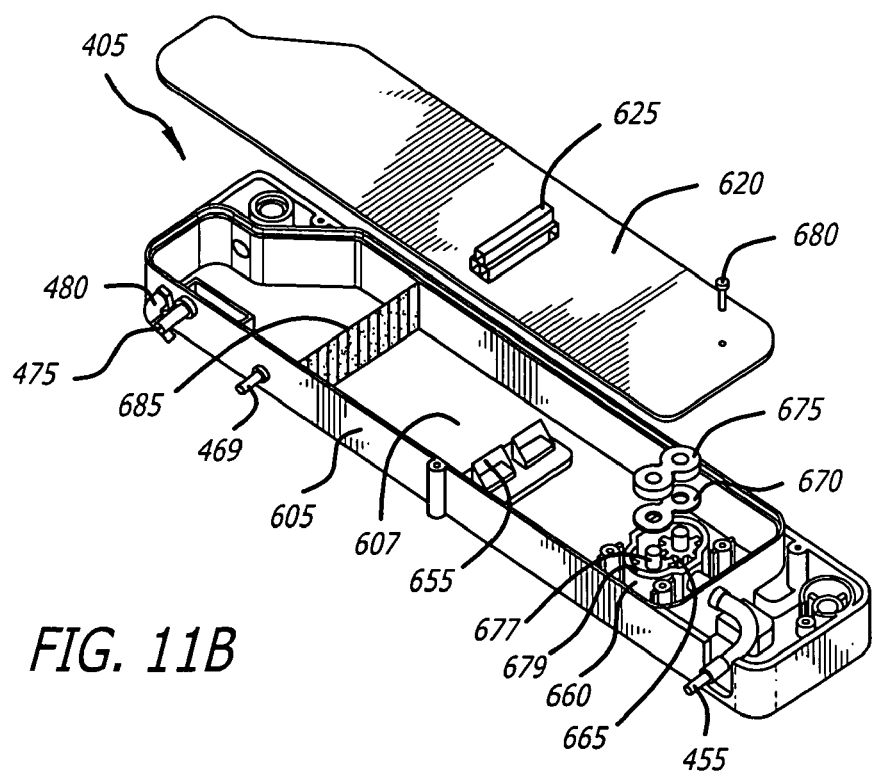
FIG. 11B is an exploded perspective view of the cassette portion of the embodiment of FIG. 9 showing a view of the internal structure of the cassette portion.

FIGS. 11A and B depict additional detail of an exemplary embodiment of the cassette section 405. Referring to FIG. 11A, the cassette section 405 is shown in the reverse orientation in which it is inserted into the control unit (FIG. 2). Cassette section 405 includes a cassette block 605 which, as is seen in FIG. 11B, has side walls that form a reservoir 607. Also visible on the bottom surface of cassette block 605 in FIG. 11A is a window 615 which provides for transmission of light beams into the reservoir for use in determining the fluid level within the reservoir 607. Pump coupler 610 is also disposed on the bottom surface of the cassette block 605, and is configured to couple to pump driver 68 (FIG. 2) to drive the secondary fluid circuit pump.

The top side of cassette block 605 is closed by cover 620. Cover 620 is typically opaque, and includes a mirror 625 disposed on an inside surface of the cover 620. Mirror 625 forms part of a fluid level sensor that is used to determine the level of secondary circuit fluid within reservoir 607. Also shown are pump seal 630 and pump shaft bushings 635, which will be described in more detail with reference to FIG. 11B.

FIG. 11B depicts the cassette section 405 in a right side up orientation so as to facilitate discussions of additional details of the structure and components of the cassette section 405. As described above, the sides walls of cassette block 605 and the cover 620 form a secondary fluid circuit reservoir 607 within cassette section 605. A prism 655 which forms a portion of the above described level sensor is mounted on an inner surface of the cassette block, and is in light communication with window 615 disposed on the top surface of cassette block 605.

In an alternative embodiment, two prism may be used to provide a redundant system. In such an arrangement, the controller may also have two processors, one main processor and a safety processor. The main processor monitors the first prism, and the safety processor monitors the second prism. The monitoring of the prisms may be timed by the processors such that the main processor should detect any abnormalities before the safety processor does. Thus, an alert may be sent to the user and the pump will stop. In this case, the pump may be restarted. If the abnormality is not corrected and is detected by the safety processor, the pump may be stopped and require intervention to determine the cause of the abnormality before treatment may proceed. Alternatively, both safety systems may function simultaneously and with equal priority, so that a low level indicator by either one will trigger a signal to the user such as an alarm, or will stop the pump.

Disposed within the reservoir 607 is secondary fluid circuit pump 660. In the depicted embodiment, pump 660 is a gear pump having a pair of pumping gears 665 each mounted on a pump shaft 677 disposed within a pump body 679. A backing plate 670 holds shafts 677 in place within the pump, and a height compensator 675, which is typically formed from a compressible material, such as a biocompatible plastic such as, for example, silicon, is disposed on the shafts between the backing plate 670 and the end of the shafts. The height compensator supplies pressure onto the pump gears to hold the gears in place while allowing some movement of the gears so they may freely rotate. Cover 620, which is shown inverted in FIG. 11B, is held in place on cassette block 605 to form reservoir 607 using suitable connectors 680.

Also disposed in reservoir 607 is an air trap 685. Air trap 685 is made from a porous material that allows secondary fluid to flow through the air trap, but blocks the flow of air. Air trap 685 may be formed from any material that preferentially allows fluid to flow but blocks the flow of air, for example, such as a semi permeable membrane or a foam block. Although the air trap may be omitted in some embodiments of the present invention, use of air trap 685 is advantageous as it provides a means for trapping air bubbles, either large of small, entrained in the secondary circuit fluid before the fluid enters the secondary circuit pump.

In an alternative embodiment, where the cassette reservoir is sufficiently isolated using luer lock connectors and check valves, the cassette reservoir may be pre-filled with secondary fluid. Providing such a pre-filled reservoir would eliminate the need to prime the secondary fluid circuit with secondary fluid before operating the pump. In such an arrangement, a fluid used to fill the fluid pathways of the catheter could be made up by attaching the priming line to a fluid source, if necessary.

It will be understood that the pump 660 may be located on the output side of the heat exchanger's secondary fluid circuit to push secondary fluid through the catheter. Alternatively, the pump 660 may also be located on the inlet side of the heat exchanger's secondary fluid circuit.

In an alternative embodiment, a suitably flexible cooling balloon can be mounted on the catheter such that pulsations in the secondary fluid caused by the pump result in fluctuation of the balloon. Such fluctuation of the balloon may be advantages in promoting better heat transfer between a patient's blood and the cooling fluid in the balloon by inducing turbulence in the blood flow adjacent to the surface of the balloon.

Safety Systems

As described previously, the reservoir section can be provided with a means to monitor the amount of heat exchange fluid that is in the system, more specifically an optical means for detecting the level of fluid contained within the fluid reservoir. Since the secondary fluid is a biocompatible fluid and the volume of the external source is only about 250 ml, it is not expected that fluid leakage into the patient will be problematic. It would be undesirable, however, to have the fluid level fall so low that air is pumped into a patient. Therefore the heat exchange fluid supply system of the invention is designed to detect the level of the fluid in the system so that a warning or other measure can be instituted if the system becomes unacceptably low. As shown in FIGS. 11A and B, a pair of prisms 655 are mounted to the cassette block 605 each having a corresponding beam source and beam, are utilized to form a fluid level sensor. Each prism 655 will have a corresponding beam source and sensor mounted on the control unit at a location adjacent to the prism.

As seen in FIG. 11A, the transparent window 615 disposed in the bottom surface of the cassette block 605 allows for optical monitoring of the fluid level in the reservoir 607. An adjacent beam source and sensor would also be provided for the second prism 655, if present.

Typically, the beam source(s) and sensor(s) would be positioned on the control unit at a location so as to access the interior of reservoir 607 through the window 615. The prisms 655 have a diffraction surface and may be molded or machined separately using a material such as polycarbonate and then affixed within the reservoir section, or they may be machined as part of the section. Again, although only one prism is needed for the fluid level detection method to function, it may be desirable to include a second redundant prism described below.

The second prism/source/sensor is redundant and functions to monitor the same fluid level as the first prism but operates as a safety mechanism in the even the first prism/source/sensor fails to function properly. Alternatively, one of the prisms may also have a "high level" sensing system that can be used to signal the control unit when the fluid in the reservoir reaches a certain high level. This is useful, for example, when a valved-priming system is used and detection of a high or full level is needed to determine when to activate the valve to stop the priming sequence. If desired, both high level and low level sensors can be employed on each prism. The sensors will generate a signal indicating that either there is or is not fluid at the level of the optical beam. If the optical beam source and sensor are positioned or the optical beam is directed near the top of the tank, the indication that the fluid has reached that level will trigger the appropriate response from the control system, for example to terminate a fill sequence. On the other hand, if the sensor is positioned or optical beam directed to sense the fluid level on the bottom of the tank, then the fluid level detector is configured to detect a low fluid level and can generates a signal representing such low level. The controller can then be configured to respond to this signal indicative of a low level of fluid in the reservoir. For example, the controller can be designed to be responsive to this signal such that it controls the secondary circuit pump to stop pumping when a low fluid level is detected, so that air will not be pumped into the heat exchange catheter. In addition, an alarm may sound and an alarm display, such as the display 200 of FIG. 5C, may be activated to alert the operator to the low fluid level condition.

In a preferred embodiment of the present invention, several levels of safety redundancy are provided to prevent failure of the system, and potential injury to the patient. First, two microprocessors may be provided and constantly monitored for agreement. If one fails, the system alarms and shuts. Secondly, two or more patient sensors may be provided and monitored for agreement. They are sampled frequently by the controller and if the values do not agree, as with the microprocessor, the system alarms and shuts down. Likewise, two or more fluid level sensors for the heat exchange circulation path desirably agree for redundancy. Still further, two or more temperature sensors for the heat exchange medium could be provided and monitored for agreement. In short, various redundant subsystems of the overall system ensure proper operation and the feedback therefrom is used to shut off the system if necessary.

In another preferred embodiment of the invention, the reservoir 607 section is provided with a means to detect when the fluid reservoir is too low. Typically, an optical beam source would begin operation after the reservoir fills with fluid. In operation, the optical beam source produces an optical beam that is directed into the prism from the bottom and is internally reflected one or more times within the prism at its surface interface with the fluid and back to the optical beam sensor. As long as fluid is in the reservoir, the sensor will observe a reflected light beam and the pump will continue to operate, moving fluid through the heat exchange cassette and catheter. However, if the fluid level drops below the upper reflective surfaces of the prism, thus changing the reflective index at that internal surface, the sensor then will not observe a reflected light beam. When no such reflected beam is received, the system sounds an alarm and ceases to pump.

Additional safety systems that are contemplated by the invention include bubble or air-in-line detectors at various locations on the conduits to detect any bubbles or entrained air that may be pumped into the fluid system and temperature monitors that may signal if a portion of the system, or the fluid, is at a temperature that is unacceptably high or low. Moreover, the bubble or air-in-line detectors may also be configured to indicate whether an acceptable level of fluid is present within a fluid circuit. A detector to indicate whether the fluid sensor optical beam sources are operational may be supplied, for example by placing a detector located to detect the optical beam initially when the system is turned on but there is insufficient fluid in the reservoir to cause the beam to diffract back to the detector. The control unit depicted in FIGS. 1,2 and 5 provide for multiple patient temperature sensors. A warning may sound, and the system may shut down, if the temperature signal from the two different sensors are dramatically different, indicating that one of the sensors, perhaps the one driving the control of the system, is misplaced, is not functioning, has fallen out or the like. Other similar safety and warning systems are contemplated within the scope of the system of the invention.

It should also be understood, in accordance with the present invention, that the controller processor may be configured to simultaneously respond to multiple sensors, or to activate or de-activate various components such as several heat exchangers. In this way, for example, a controller might heat blood that is subsequently circulated to the core body in response to a sensed core body temperature that is below a target temperature for the core, and simultaneously activate a second heat exchanger to cool blood that is directed to the brain region in response to a sensed brain temperature that is above a target temperature for the brain. It may be that the sensed body temperature is at the target temperature and thus the heat exchanger that is in contact with blood circulating to the body core may be turned off by the controller, while at the same time the controller continues to activate the second heat exchanger to cool blood that is directed to the brain region. Any of the many control schemes that may be anticipated by an operator and programmed into the control unit are contemplated by this invention.

Figure 12:
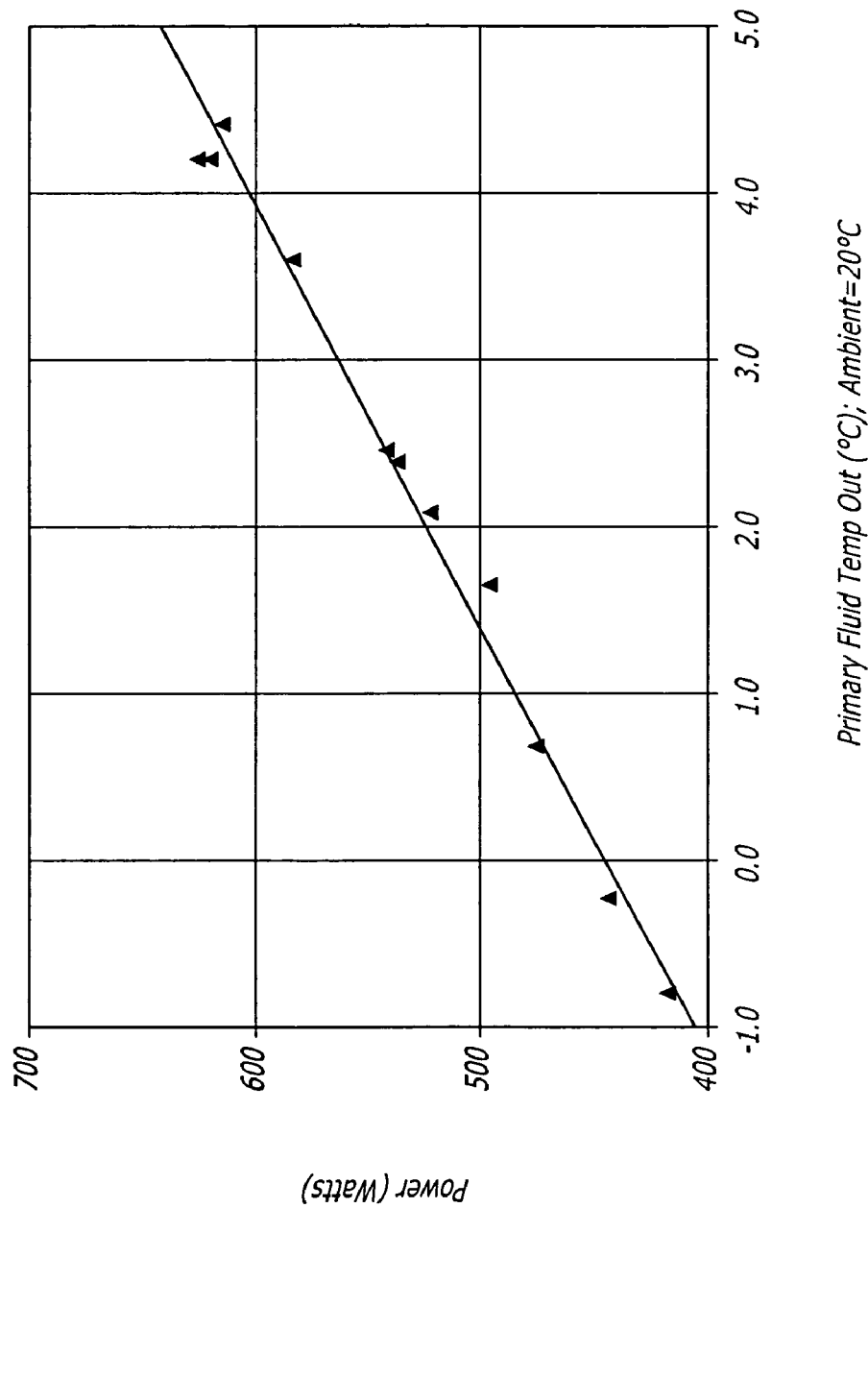
FIG. 12 is a graphical illustration of the heat extraction (power) capability of one embodiment of the present invention as a function of primary fluid temperature.

One advantage of the various embodiments of the system of the present invention is that it provides for the exchange of a large amount of heat between a patient's blood and the cooling circuits. In order to ensure that a patient's temperature may be lowered as rapidly as possible, and then maintained, it has been found to be desirable to maintain the primary fluid circuit at a temperature in the range of 0-5 degrees centigrade against a thermal load of greater than 400 watts. However, as those skilled in the art will understand, maintaining the primary fluid temperature at such a level is difficult to accomplish. FIG. 12 is a graphical representation showing how one embodiment of the present invention performed. This graph shows that the embodiment tested was able to maintain a primary fluid temperature of less than 1.5 degrees centigrade under a power load of 500 watts.

Figure 13:
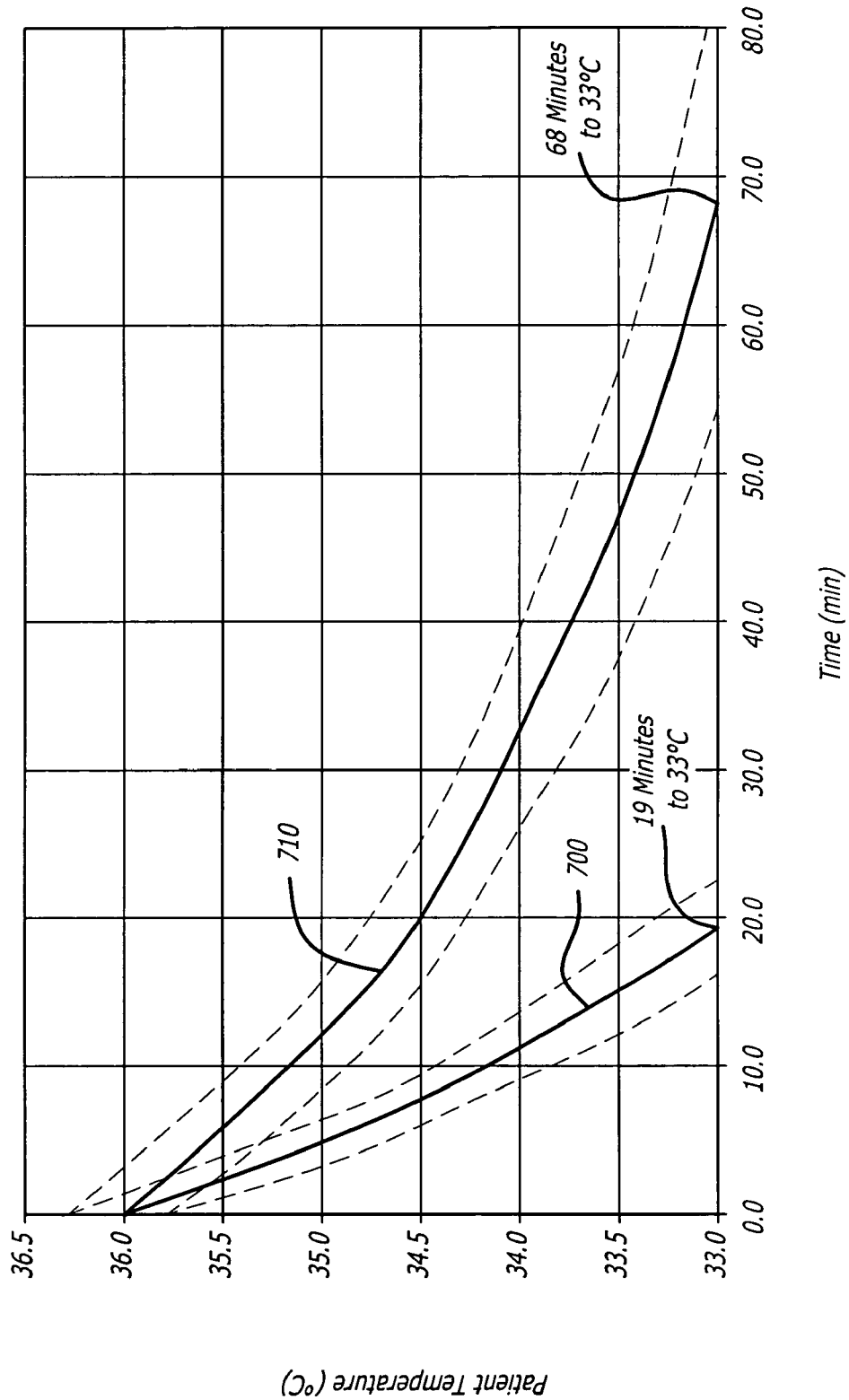
FIG. 13 is a graphical comparison of the temperature reducing capability of an embodiment of the present invention compared to the temperature reducing capability of a prior system.

FIG. 13 is a graphical representation illustrating the performance of one embodiment of the present invention compared to the performance of prior cooling system when used to cool patients. Line 700 was derived using the embodiment of the present invention, and shows how patients were cooled to 33 degrees centigrade in an average of 19 minutes. This contrasts with the prior system, depicted by line 710, which required 68 minutes on average to cool a patient to 33 degrees centigrade. The dashed lines in FIG. 13 depict the 95% confidence interval around the data used to derive the lines 700, 710.

Another advantage of the system of the present invention is that the ability to extract large amounts of heat from the primary cooling loop provides for reduced time for the system to begin removing large amounts of thermal energy from the patient. For example, when needed, the primary cooling loop can be cooled to its target temperature of less than 3 degrees centigrade in 5 minutes or less. Such rapid cooling may be needed in an emergent situation where fast cooling of a patient is desired but where use of such a system was not anticipated.

A further advantage of the system of the present invention is that all of the portions of the system that are in contact with the patient may be disposable, but substantial and relatively expensive portions of the system are reusable. Thus, the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross-contamination will occur between patients because all those elements are disposable. The pump driver, the electronic control mechanisms, the heat exchanger, and the manual input unit, however, are all reusable for economy and convenience. Desirably, as illustrated, all of these re-usable components are housed within a single control unit that may be operated by a single operator in the surgical or general wards of a hospital or other care giving institution. Likewise, the various sensors distributed around body and along the catheter may be disposable, but the controller processor to which they attach is re-usable without the need for sterilization.

In another embodiment of the present invention, as shown in FIG. 6, check valve 286 may be included in the primary fluid circuit to control the pressure within the primary fluid circuit should the outlet side of the primary fluid circuit be disconnected. In some embodiments, the primary fluid circuit pump is capable of pumping the primary fluid at pressures that greatly exceed a preselected safety threshold. For example, the pump may be capable of reaching pressures of 50 psi or more. To provide further safety to the patient, the check valves in the primary fluid circuit may be chose so as to prevent the pressure within the primary circuit from exceeding a pressure that has been determined to be safe, such as, for example, 35 psi. This prevents the heat exchanger from ever being exposed to a pressure that might cause a failure of the primary fluid circuit within the heat exchanger. This provides for increased safety for the patient, since the pressure limit prevents the possibility of a catastrophic rupture heat exchanger fluid circuits and thus prevents the possibility of circulation of primary fluid, which may be a material such as alcohol or propylene glycol or the like, into the secondary fluid circuit, through the catheter, and into the patient.

The unique combination of fluid lines, connectors and valves provide many advantages over prior art systems. For example, where the primary fluid connectors of the cassette include releasable couplers which fluidly seal, the cassette may be shipped with the primary fluid circuit of the cassette full of primary cooling fluid. In another embodiment, the secondary fluid circuit of the cassette may be pre-filled with secondary cooling fluid and sterilized, thus eliminating, or at least substantially reducing, the amount of time and effort needed to prime the secondary fluid circuit.

It will also be appreciated by those of skill in the art that the system described herein may be employed using numerous substitutions, deletions, and alternatives without deviating from the spirit of the invention as claimed below. For example, but not by way of limitation, the primary and secondary fluid pathways in the heat exchange plate may be a bellows, tube in tube, fan folded sheet, plate, coil or other suitable configuration, or the sensors may sense a wide variety of body locations and other parameters may be provided to the processor, such as temperature or pressure. Further, the in-dwelling heat exchanger at the end of the catheter may be any appropriate type, such as a non-balloon heating/cooling element. An appropriate pump might be provided that is a screw pump, a gear pump, a diaphragm pump, a peristaltic roller pump, or any other suitable means for pumping the heat exchange fluid. All of these and other substitutions obvious to those of skill in the art are contemplated by this invention.

Another embodiment of the present invention is configured to accept supplemental cooling devices that may be used to supplement the cooling of the primary fluid circuit, the secondary cooling circuit, or both. In one embodiment, the supplemental cooling device comprises a vessel having each end sealed with an end cap. The vessel may be cylindrical, configured as a flat plate, or other suitable configuration. The interior of the vessel between the two end caps defines a chamber filled with a cooling medium, which may be a liquid, such as water, a gel, or a solid such as ice or other frozen material. An inlet tube extending through one of the end caps carries a first quick-disconnect fastener for detachably coupling the inlet tube in fluid communication with a fluid source, such as the primary or secondary fluid circuit, and an outlet tube extending through the other end cap, terminated by a second quick-disconnect for detachably coupling the outlet tube in fluid communication with the primary or secondary fluid circuits. As fluid from the primary or secondary fluid circuits enters the inlet tube, heat energy in the fluid is absorbed by the cooling medium, and thus the temperature of the fluid flowing through the fluid circuit is further cooled by the cooling device. This supplemental cooling provides for an increased rate of temperature reduction in a patient, which may be beneficial in certain situations. Moreover, if the amount of cooling required exceeds the cooling capacity of the main heater/cooler, even with the addition of one supplemental cooling device, additional supplemental cooling devices may be coupled into the primary or secondary fluid circuits as desired. Further, the quick-disconnect couplings allow for replacement of a supplemental cooling device that has absorbed as much heat energy as it can with a fresh supplemental cooling device when necessary. Alternatively, other stored energy sources such as compressed or liquefied gas, or endothermic reactive chemicals, may be used as supplemental cooling sources. Additionally, the system may also be configured with supplemental heating sources to augment the heating ability of the system to address situations where a patient requires warming at a higher rate than can be provided by a TE or resistive heating element alone.

While particular embodiments of the invention have been described above for purposes of illustration, it will be evident to those skilled in the art that numerous variations of the above-described embodiments may be made without departing from the invention as defined in the appended claims.

We claim:

1. A system for adjusting the temperature of a patient, comprising:
   a primary fluid circuit, the circuit including:
     a primary fluid circuit pump,
     heater/cooler,
     primary fluid circuit lines connecting the primary fluid circuit pump to the heater/cooler such that a continuous flow path for circulating primary fluid from the pump to the heater/cooler and back to the heater/cooler is formed;

access points in the primary fluid circuit, the access points fluidly connecting the primary fluid circuit to a primary fluid circuit side of a heat exchanger, the heat exchanger also having a secondary fluid circuit side;

a heat exchange catheter insertable within a patient, the catheter configured to increase, decrease or maintain the temperature of the patient;

a secondary fluid circuit for flowing secondary fluid through the secondary circuit side of the heat exchanger and the heat exchange catheter, the secondary fluid circuit including a secondary fluid circuit pump for flowing a secondary heat exchange fluid through the secondary fluid circuit to the heat exchange catheter and back through the secondary fluid circuit to the secondary fluid pump;

at least one fluid sensor configured to provide a signal representative of a temperature of the primary or secondary fluid circuit;

a patient sensor configured to provide a signal representative of a temperature of the patient;

a controller configured to receive the signals from the patient sensor and the primary fluid sensor and being responsive to the signals to control the heater/cooler to adjust the temperature of the fluid flowing within the fluid circuits.

2. The system of claim 1, wherein the controller includes a microprocessor configured to be responsive to sensors and to provide control signals as needed to control the operation of the system.

3. The system of claim 2, further comprising:

a power supply for supplying power to the system, including the heater/cooler;

controller circuitry for controlling the operation of the system, the controller circuitry including means for determining if the power supply is operative and operating within parameters determined to be appropriate, means for monitoring the operation of the system, means for determining an error state of the monitored system, and means for alerting an operator of the presence of an error state.

4. The system of claim 2, further comprising a secondary fluid reservoir in fluid communication with the secondary fluid circuit.

5. The system of claim 4, wherein the secondary fluid reservoir includes an air trap disposed between an inlet to the reservoir and the secondary fluid circuit pump.

6. The system of claim 5, wherein the air trap is a semi-permeable member permitting at least a portion of the secondary fluid to flow through the semi-permeable member.

7. The system of claim 5, wherein the air trap is formed from foam.

8. The system of claim 1, wherein the controller controls the heater/cooler to drive the temperature of the fluid in the primary fluid circuit towards a predetermined temperature prior to fluidly connecting the heat exchanger to the primary fluid circuit.

9. The system of claim 1, wherein the controller controls the heater/cooler to drive the temperature of the fluid in the primary fluid circuit towards a predetermined temperature prior to initiation of treatment of a patient.

10. The system of claim 1, wherein the primary fluid circuit includes temperature sensors disposed in the primary fluid circuit, the temperature sensors providing signals representative of the temperature of the primary fluid passing through the access points flowing into and out of the primary fluid circuit side of the heat exchanger.

11. The system of claim 10, wherein the temperature difference between the fluid flowing into and out of the primary fluid circuit side of the heat exchanger is proportional to the heat exchange being delivered to the secondary fluid circuit, and is representative of the heat exchange being delivered to the patient.

12. The system of claim 10, wherein the controller is responsive to the signals provided by the temperature sensors to determine the difference in the temperature of the primary fluid flowing into and out of the access points, and to provide an alert if the determined difference is indicative of a problem condition.

13. The system of claim 10, wherein the controller is responsive to the signals provided by the temperature sensors to provide an alert if the signals are indicative of a problem condition.

14. The system of claim 10, wherein a duty cycle of the heater/cooler is reduced when the controller determines that the sensed temperature is within a predetermined range for a predetermined amount of time.

15. The system of claim 1, further comprising a primary fluid reservoir in fluid communication with the primary fluid circuit.

16. The system of claim 1, wherein the secondary fluid circuit contains a particulate filter.

17. The system of claim 16, wherein the particulate filter is a semi-permeable member permitting at least a portion of the secondary fluid to flow through the semi-permeable member.

18. The system of claim 16, wherein the particulate filter is formed from foam.

19. The system of claim 16, wherein the particulate filter is a screen.

20. The system of claim 1, further comprising a level detector disposed in the secondary fluid circuit to detect a level of the fluid within the secondary fluid circuit, the level detector providing a signal representative of the level of fluid in the secondary fluid circuit to the controller.

21. The system of claim 20, wherein the level detector is disposed in cooperation with the secondary fluid reservoir to detect a level of the fluid within the secondary fluid reservoir.

22. The system of claim 20, wherein the controller sends a start signal to the secondary fluid pump in response to a signal from the level detector representative of a predetermined fluid level.

23. The system of claim 20, wherein the controller sends a stop signal to the secondary fluid pump in response to a signal from the level detector representative of a predetermined low fluid level.

24. The system of claim 20, wherein the level detector is a bubble detector.

25. The system of claim 20, wherein the level detector is an air in line detector.

26. The system of claim 1, wherein the secondary fluid circuit pump and secondary fluid reservoir and heat exchanger are included in a cassette configuration that is provided in a sterile condition.

27. The system of claim 26, further comprising a reusable housing in which are disposed the primary fluid reservoir, primary fluid circuit pump, microprocessor and a secondary fluid circuit pump motor, the housing being configured to removably receive the cassette such that the secondary fluid circuit pump releasably engages the secondary fluid circuit pump motor.

28. The system of claim 26, wherein the cassette and catheter may be disconnected from the primary fluid circuit and connected to a different primary circuit without compromising sterility or fluid isolation of the secondary fluid circuit of the cassette and catheter.

29. The system of claim 1, wherein the access points include releasable couplers for releasably coupling the heat exchanger to the primary fluid circuit.

30. The system of claim 29, wherein the releasable couplers fluidly seal when not connected to the primary fluid circuit to minimize primary fluid loss from the primary fluid circuit side of the heat exchanger and the primary fluid circuit.

31. The system of claim 1, wherein the primary fluid circuit further comprises a check valve for controlling a fluid pressure within the primary fluid circuit such that the fluid pressure does not exceed a predetermined value.

32. The system of claim 1, wherein a duty cycle of the heater/cooler is reduced when the controller determines that a sensed temperature is within a predetermined range.

33. The system of claim 1, wherein a duty cycle of the primary and/or secondary fluid pump is reduced when the controller determines that a sensed temperature is within a predetermined range.

34. The system of claim 1, wherein a duty cycle of the primary and/or secondary pump is reduced when the controller determines that demand for patient temperature change is reduced.

35. The system of claim 1, wherein the primary fluid circuit is configured such that the majority of volume of primary fluid contained with the heat exchanger is recovered to a primary fluid reservoir prior to disconnection of the heat exchanger from the primary fluid circuit.

36. The system of claim 1, wherein the heat exchanger is provided to the operator with the primary fluid side pre-filled with primary fluid.

37. The system of claim 36, wherein the means includes a sensor configured to sense an electrical characteristic of the fluid within the fluid circuit.

38. The system of claim 1, wherein the heat exchanger is provided with the secondary fluid side pre-filled with secondary fluid.

39. The system of claim 1, wherein the primary fluid circuit includes a means for maintaining an electrical conductivity at a value below a predetermined value.

40. The system of claim 1, further comprising a priming fluid circuit for providing secondary heat exchange fluid to the secondary fluid circuit.

41. The system of claim 40, wherein the priming fluid circuit includes a prime line and a vent line, at least of one of the prime line and vent line having a valve, and at least one sensor for determining when the secondary circuit is sufficiently filled with fluid.

42. The system of claim 41, wherein at least one of the valves in the prime line and vent line is a clamp that engages the line to obstruct fluid flow in the line.

43. The system of claim 42, wherein the at least one of the valves in the prime line and vent line are controlled by the controller to initiate and complete filling the secondary fluid circuit with secondary fluid.

44. The system of claim 1, wherein the access points are configured to receive primary circuit fluid to fill a primary fluid reservoir.

45. The system of claim 1, wherein the controller controls the temperature of the primary fluid circuit at a level sufficient to prevent freezing of the secondary fluid in the secondary fluid circuit.

46. The system of claim 1, wherein the primary fluid side of the heat exchanger is a primary intermediate fluid pathway and the secondary fluid side of the heat exchanger is a secondary intermediate fluid pathway.

47. The system of claim 46, wherein the primary fluid circuit has a volume, and the volume is increased when the primary intermediate fluid pathway is placed in fluid communication with the primary fluid circuit.

48. The system of claim 1, wherein the secondary side of the heat exchanger has releasable couplings for coupling and uncoupling the secondary side of the heat exchanger with a heat exchange catheter circulating heat exchange fluid therethrough.

* * * * *

UNITED STATES PATENT AND TRADEMARK OFFICE
CERTIFICATE OF CORRECTION

| | |
|---|---|
| PATENT NO. | : 7,806,915 B2 |
| APPLICATION NO. | : 11/413564 |
| DATED | : October 5, 2010 |
| INVENTOR(S) | : David J. Scott et al. |

It is certified that error appears in the above-identified patent and that said Letters Patent is hereby corrected as shown below:

Column 5, line 63, before "patient," insert --the--.

Column 8, line 25, delete "for" and insert instead --or--.

Column 9, line 27, delete "with" and insert instead --within--.

Column 17, line 32, before "processor" insert --the--.

Column 20, line 65, after "above" insert --a--.

Column 22, line 2, delete "beginning" and insert instead --begin--.
            line 11, after "which" insert --can--.
            line 48, delete "should".

Column 27, line 15, delete "is".
            line 56, delete "though" and insert instead --through--.

Column 28, line 16, delete "though" and insert instead --through--.

Column 30, line 14, delete "of" and insert instead --or--.
            lines 34-35, delete "advantages" and insert instead --advantageous--.

Column 31, line 8, delete "even" and insert instead --event--.

Column 32, line 53, after "invention" insert --is--.

Column 33, line 40, delete "chose" and insert instead --chosen--.
            line 47, after "rupture" insert --of the--.

Signed and Sealed this
Twenty-third Day of August, 2011

David J. Kappos
*Director of the United States Patent and Trademark Office*

CERTIFICATE OF CORRECTION (continued)
U.S. Pat. No. 7,806,915 B2

Column 37, line 28, delete "with" and insert instead --within--.